United States Patent
Ota et al.

(10) Patent No.: US 8,509,512 B2
(45) Date of Patent: Aug. 13, 2013

(54) EXAMINATION METHOD, EXAMINATION APPARATUS AND EXAMINATION PROGRAM

(75) Inventors: Yoshihide Ota, Osaka (JP); Noriyuki Kato, Nara (JP)

(73) Assignee: Omron Corporation, Kyoto (JP)

( * ) Notice: Subject to any disclaimer, the term of this patent is extended or adjusted under 35 U.S.C. 154(b) by 737 days.

(21) Appl. No.: 12/649,997

(22) Filed: Dec. 30, 2009

(65) Prior Publication Data

US 2010/0172561 A1     Jul. 8, 2010

(30) Foreign Application Priority Data

Jan. 8, 2009    (JP) ................................ P2009-002813

(51) Int. Cl.
    *G06K 9/00*         (2006.01)

(52) U.S. Cl.
    USPC ............................................ 382/131; 378/21

(58) Field of Classification Search
    USPC ........................................ 378/4–27; 382/131
    See application file for complete search history.

(56) References Cited

U.S. PATENT DOCUMENTS

| | | | |
|---|---|---|---|
| 4,386,812 A | | 6/1983 | Anderson |
| 6,256,370 B1 * | | 7/2001 | Yavuz ............................. 378/22 |
| 2005/0074088 A1 * | | 4/2005 | Ichihara et al. ................. 378/58 |

FOREIGN PATENT DOCUMENTS

| | | |
|---|---|---|
| CN | 1595124 A | 3/2005 |
| JP | 2003-344316 A | 12/2003 |
| JP | 2005-121633 A | 5/2005 |
| JP | 2005-121633 A | 5/2005 |
| JP | 2006-292465 A | 10/2006 |
| JP | 2009-115462 A | 5/2009 |
| JP | 2009-162596 A | 7/2009 |
| JP | 2010-002221 A | 1/2010 |
| WO | WO 2009/078415 A1 | 6/2009 |

OTHER PUBLICATIONS

Japanese Patent Office action on application 2009-002813 mailed Mar. 26, 2013; pp. 1-2.

* cited by examiner

*Primary Examiner* — Hoon Song
(74) *Attorney, Agent, or Firm* — Foley & Lardner LLP

(57) ABSTRACT

This invention provides an examination method, an examination apparatus, and an examination program capable of performing the examination corresponding to the type or the like of the site to be examined and capable of reducing the examination time when examining the substrate. The X-ray is output from an X-ray source, and the X-ray that transmitted the substrate to be examined is photographed as an X-ray perspective image in an FPD (Flat Panel Detector). The photographing for generating the reconstruction data by X-ray CT is performed at the positions on the virtual circle having the optical axis of the X-ray source as an axis, similar to the photographing for generating the reconstruction data by tomosynthesis. Thus, in generating the reconstruction data by X-ray CT, the data is converted so that each image rotates using affine conversion with the center of each X-ray perspective image as an axis according to the rotation position on the virtual circle as if the X-ray perspective images obtained at the respective positions are photographed at the positions, and then the filtering process is performed.

8 Claims, 20 Drawing Sheets

BACK PROJECTION

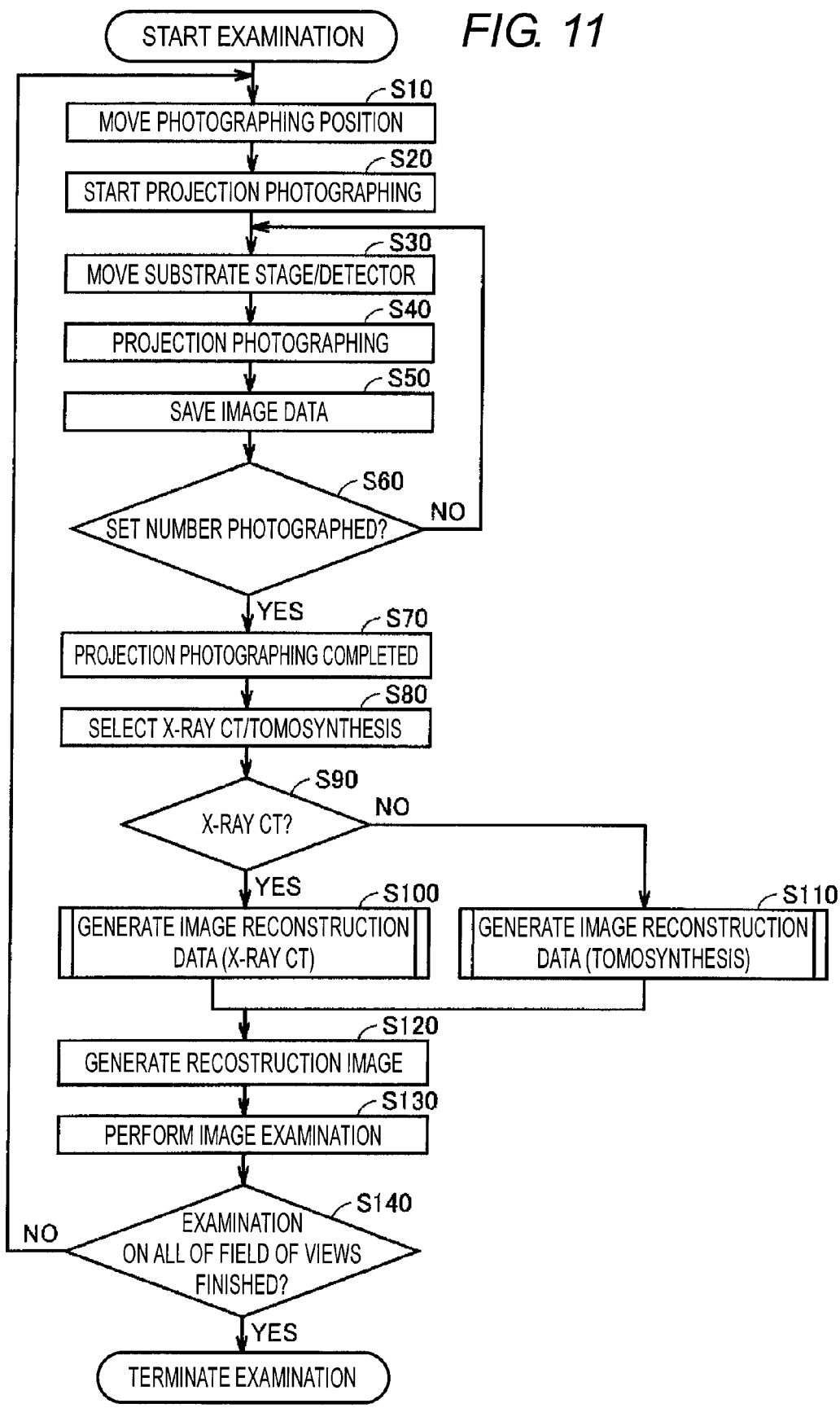

EXAMINATION METHOD, EXAMINATION APPARATUS AND EXAMINATION PROGRAM

This application is based on Japanese Patent Application No. 2009-002813 filed with the Japan Patent Office on Jan. 8, 2009, the entire content of which is hereby incorporated by reference.

BACKGROUND OF THE INVENTION

1. Technical Field

The present invention relates to examination methods, examination apparatuses, and examination programs, and in particular, to an examination method, an examination apparatus, and an examination program for performing examination related to an examining object by generating an X-ray tomographic image.

2. Related Art

An X-ray CT (Computed Tomography) is known as one example of a method of generating a tomographic image by an X-ray with a component mounting substrate as a target, and examining a joint state of a component side electrode and a substrate, an internal structure of a solder electrode, and the like using the generated image.

Japanese Unexamined Patent Publication No. 2006-292465 discloses one example of a technique related to the examination of a substrate using the X-ray CT.

With reference to FIG. 18A, Japanese Unexamined Patent Publication No. 2006-292465 discloses a technique of moving a bump on a substrate 920 to be examined to a field of view of an X-ray detector 950, and acquiring an X-ray image. The X-ray detector 950 is rotatable on a circumference of a radius R having an axis A extended in a vertical direction from a focus F of an X-ray generator 900 as a center. α is an inclination angle of the X-ray detector 950 with respect to the axis A. Here, the rotating operation of the X-ray detector 950 is performed, and the substrate 920 is moved within an X-Y plane so as to include the bump, which is the examination target, within the field of view of the X-ray detector 950 after the rotation. The field of view region FOV of the X-ray detector 950 is moved with the position in a Z-axis direction of the substrate 920 fixed, and the X-ray image is photographed by the X-ray detector 950 in a plurality of states of the field of view region FOV. The X-ray image is then photographed for a plurality of field of view regions FOV within the X-Y plane while changing the position in the Z-axis direction. A reconstruction calculation of a three-dimensional image is performed using the X-ray image for each of a plurality of field of view regions FOV obtained for a plurality of Z-axis directions.

In such photographing for the X-ray CT, the field of view region FOV of the X-ray detector 950 changes from FOV1 to FOV4 rotating with O, which is a correspondence point on the vertical direction of the focus F of the X-ray generator 900, as the center within the X-Y plane, as shown in FIG. 18B.

A method of generating a tomographic image of the substrate includes a method of generating a tomographic image of the substrate through tomosynthesis, that is, a method of generating a tomographic image of the substrate easier than the X-ray CT. For instance, Japanese Unexamined Patent Publication No. 2005-121633 discloses generating the tomographic image through such method. In Japanese Unexamined Patent Publication No. 2005-121633, an X-ray source 900 is arranged with an optical axis AX thereof facing upward in a perpendicular direction, an XY stage for supporting a substrate serving as an examining object 921, is arranged on the upper side thereof, and an XY stage for supporting a two-dimensional X-ray detector is further arranged on the upper side, with reference to FIG. 19. In FIG. 19, circular orbits R1, R2 are circular orbits having the optical axis AX (broken line) of the X-ray source 900 as a center. Each XY stage is moved along the circular orbits R1, R2 and stopped at every predetermined angle, and photographing is carried out. The images (P1 to P4) generated by each photographing are synthesized to generate the tomographic image.

As described in Japanese Unexamined Patent Publication No. 2005-121633, in the tomosynthesis photographing, each constructing point of the target plane is projected on the same coordinate of every image with a plane of a predetermined height as the target, and the relationship of the X-ray source, the X-ray detector, and the substrate in each photographing is adjusted so that each constructing point of the upper and lower planes is projected to different coordinates for every photographing. As a result, when each image is synthesized, the constructing points of the target plane are superimposed and become clear, but the constructing points of other planes become unclear. The tomographic image in which the noise is alleviated for the target plane thus can be generated.

SUMMARY

Comparing the tomographic image by tomosynthesis and the X-ray CT image, the latter image is generally superior in terms of accuracy. However, the time necessary for generating the tomographic image becomes long in the X-ray CT since the calculation is complicating. According to the tomosynthesis, however, the tomographic image can be obtained in a relatively short time since the calculation is simple. The tomographic image may contain non-ignorable noise components depending on the relationship between the shape of the site to be examined and the peripheral construction.

Due to such situation, the companies that manufacture and examine the substrate desire to selectively execute the X-ray CT and the tomosynthesis according to the type of site to be examined and the peripheral state of the site to be examined.

However, the photographing method is different for the photographing for generating the X-ray CT image and the photographing for generating the tomographic image through tomosynthesis. That is, in the X-ray CT image photographing, the orientation of a two-dimensional X-ray detector is controlled so as to rotate on a circular orbit having the optical axis of the X-ray source 900 as the center for every photographing, as indicated with positions 951 to 958, and is also controlled so as to rotate with the center of each detection region as an axis, as shown in FIG. 20A. FIG. 20A is a view of the two-dimensional X-ray detector and the X-ray source seen from the upper side in an optical axis direction of the X-ray source.

In the photographing for the image through tomosynthesis, the orientation of the two-dimensional X-ray detector is only controlled to rotate on the circular orbit having the optical axis of the X-ray source 900 as the center for every photographing, as indicated with positions 911 to 918 in FIG. 20C, and is not controlled to rotate by change in position with the center thereof as the axis.

Therefore, when switching the photographing method to the tomosynthesis photographing after the X-ray CT photographing, the orientation of the two-dimensional X-ray detector indicated as region 958 in FIG. 20A needs to be rotated to a starting position of the tomosynthesis photographing, as shown in FIG. 20B, so as to resolve the twist of the connected with cable to the two-dimensional X-ray detector. Therefore, a useless tact time is generated in the photographing for examination.

The present invention has been devised to solve the problems described above, and an object thereof is to provide a substrate examination method, an examination apparatus, and a substrate examination program capable of performing the examination corresponding to the type or the like of the site to be examined and capable of reducing the examination time when examining the substrate.

In accordance with one aspect of the present invention, the present invention relates to an examination method of imaging an X-ray output from an X-ray source and transmitted through an examination target region of an examining object with an X-ray detection unit, reconstructing a three-dimensional image of the examination target region based on imaged images, and examining the examination target region using the three-dimensional image obtained by reconstruction, the method including the steps of: changing a position of the X-ray detection unit on a virtual circle having an optical axis of the X-ray source as a center on a virtual plane, which intersects horizontally with respect to the optical axis; causing the X-ray detection unit to perform X-ray fluorography at each of a plurality of positions on the virtual circle; generating an X-ray CT (Computed Tomography) image based on the result of the X-ray fluorography by the X-ray detection unit; and generating a tomographic image of tomosynthesis based on the result of the X-ray fluorography same as the result used for generation of the X-ray CT image; wherein the step of changing the position of the X-ray detection unit includes changing the position of the X-ray detection unit so that a direction of a coordinate system of the image acquired by the X-ray detection unit remains unchanged at each of the plurality of positions on the virtual circle.

According to the examination method of the present invention, in the step of generating the X-ray CT image, data of each pixel obtained as the result of the X-ray fluorography by the X-ray detection unit is subjected to a filtering process in a direction corresponding to a rotation angle of the X-ray detection unit at each of the positions on the virtual circle having the optical axis of the X-ray source as the center.

According to the examination method of the present invention, in the step of generating the X-ray CT image, data of each pixel obtained as a result of the X-ray fluorography by the X-ray detection unit is rotated with a center pixel of the data as a center according to the rotation angle of the X-ray detection unit at each of the positions on the virtual circle having the optical axis of the X-ray source as the center, and then the filtering process is performed on the data.

According to the examination method of the present invention, in the step of generating the X-ray CT image, the filtering process in a direction corresponding to a rotation angle of the X-ray detection unit at each of the positions on the virtual circle having the optical axis of the X-ray source as the center is performed on data of each pixel obtained as a result of the X-ray fluorography by the X-ray detection unit.

According to the examination method of the present invention, the direction of the filtering process is determined for every constant angle range with respect to the rotation angle on the virtual circle.

According to the examination method of the present invention, the step of generating the X-ray CT image further includes the steps of, generating a first reconstructing pixel based on the result of the X-ray fluorography by the X-ray detection unit, generating a second reconstructing pixel by performing a filtering process on the first reconstructing pixel, and generating the three-dimensional image based on the second reconstructing pixel.

In accordance with another aspect of the present invention, the present invention relates to an examination apparatus including: a first stage for movably supporting an examining object by a movement mechanism having drive shafts in two directions; an X-ray source fixedly arranged with an optical axis directed in a perpendicular direction at an upper side or a lower side of the first stage; an X-ray detection unit; a second stage for movably supporting the X-ray detection unit by a movement mechanism having a drive shaft parallel to each drive shaft of the first stage at a position facing the X-ray source with the first stage in between; and a control unit for generating an X-ray tomographic image of an examination region of a substrate based on a detection output of the X-ray detection unit; wherein the control unit changes a position of the X-ray detection unit on a virtual circle having the optical axis of the X-ray source as a center on a virtual plane, which intersects horizontally with respect to the optical axis so that a direction of a coordinate system of the image acquired by the X-ray detection unit remains unchanged at each of a plurality of positions on the virtual circle, causes the X-ray detection unit to perform X-ray fluorography at each of the plurality of positions on the virtual circle, generates an X-ray CT (Computed Tomography) image based on the result of the X-ray fluorography by the X-ray detection unit, and generates a tomographic image of tomosynthesis based on the result of the X-ray fluorography same as the result used in the generation of the X-ray CT image.

In accordance with still another aspect of the present invention, the present invention relates to a computer readable examination program executed by a computer of an examination apparatus for imaging an X-ray output from an X-ray source and transmitted through an examination target region of an examining object with an X-ray detection unit and reconstructing a three-dimensional image of the examination target region based on imaged images, the program causing the examination apparatus to execute the steps of: changing a position of the X-ray detection unit on a virtual circle having the optical axis of the X-ray source as a center on a virtual plane, which intersects horizontally with respect to the optical axis so that a direction of a coordinate system of the image acquired by the X-ray detection unit remains unchanged at each of a plurality of positions on the virtual circle; causing the X-ray detection unit to perform X-ray fluorography at each of the plurality of positions on the virtual circle; generating an X-ray CT (Computed Tomography) image based on the result of the X-ray fluorography by the X-ray detection unit; and generating a tomographic image of tomosynthesis based on the result of the X-ray fluorography same as the result used in the generation of the X-ray CT image.

According to the present invention, the X-ray CT image and the tomographic image by tomosynthesis are generated based on the result of the same X-ray fluorography.

Therefore, a task of rotatably moving a detection region to the X-ray detection unit, and the like is not required between the photographing for generating the X-ray CT image and the photographing for generating the tomographic image by tomosynthesis. Thus, the X-ray CT and the tomosynthesis can be selected and executed according to the type of site to be examined and the state of the periphery of the site to be examined, and a step of rotating the detection region of the X-ray detection unit through execution of both the X-ray CT and the tomosynthesis can be deleted when examining the examining object such as a substrate, whereby the examination time can be shortened.

BRIEF DESCRIPTION OF THE DRAWINGS

FIG. 11 is a flowchart of a substrate examination process executed by the calculation unit of FIG. 1;

DETAILED DESCRIPTION

Hereinafter, embodiments of the examination apparatus of the present invention will be described with reference to the drawings. The same reference symbols are denoted to the same components in each figure, and the detailed description will not be repeated.

The examination apparatus of the present embodiment reconstructs tomographic images by X-ray with sites which external examination is difficult such as a pack fillet formed on the lead of the IC (Integrated Circuit) and the solder electrode constructing the BGA (Ball Grid Array) as the target, and performs examinations using the generated tomographic images. The examination apparatus of the present embodiment has a function of generating the X-ray CT image for the tomographic image, and a function of generating the tomographic image by tomosynthesis.

[1. Schematic Construction of Examination Apparatus]

Figure 1:
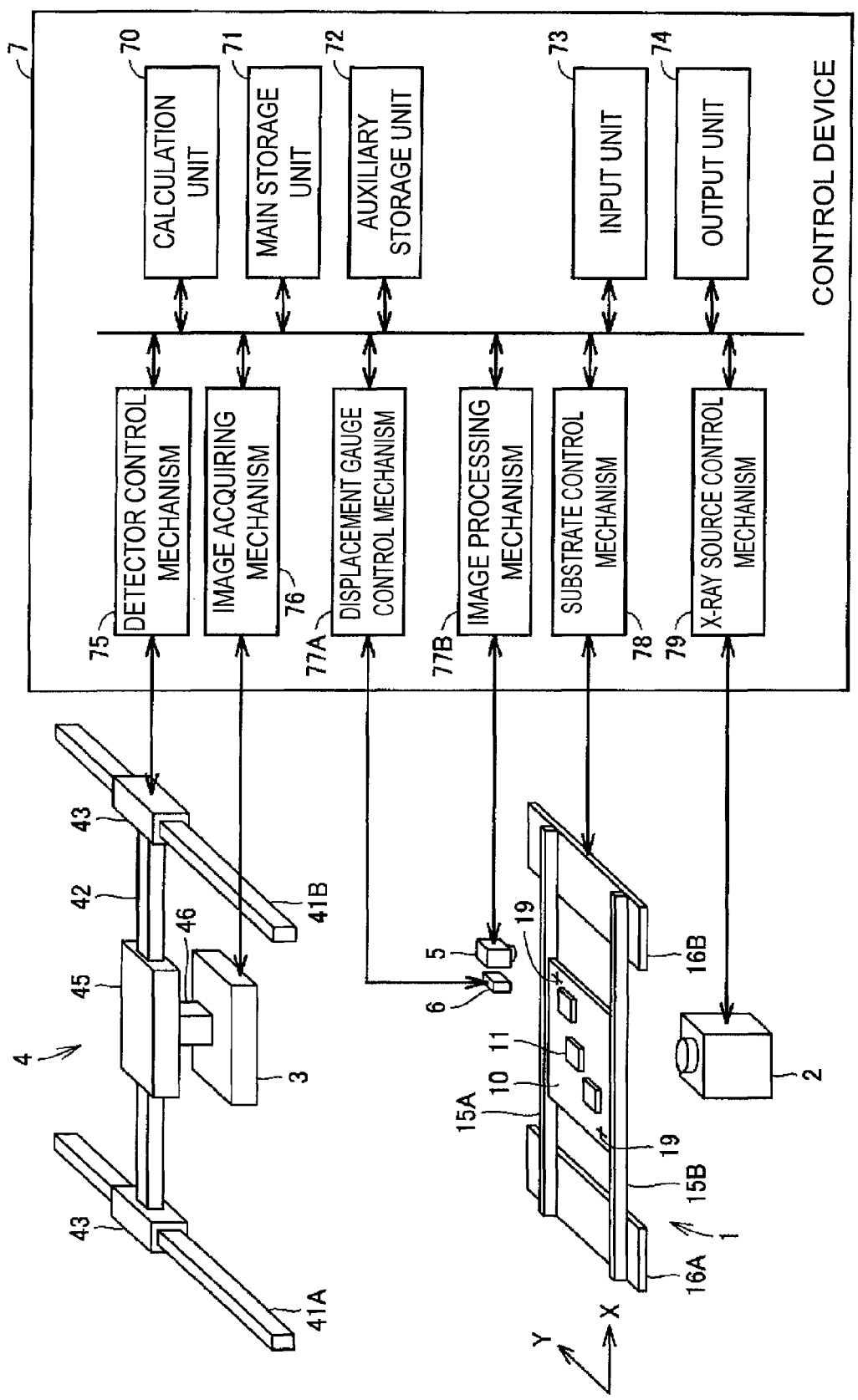
FIG. 1 is a view showing a schematic construction of one embodiment of an examination apparatus of the present invention.

FIG. 1 is a view showing a schematic construction of the examination apparatus.

With reference to FIG. 1, the examination apparatus includes a substrate stage 1 for supporting a substrate 10 to be examined, an X-ray source 2 arranged on the lower side thereof, a detector stage 4 arranged on the upper side of the substrate stage 1, and a control device 7 for entirely controlling the operation of the examination apparatus.

A state in which a part 11 is mounted on the substrate 10 is shown.

The substrate stage 1 includes a pair of conveyors 15A, 15B for supporting the substrate 10 at each end edge along a length direction (left and right direction in FIG. 1; hereinafter referred to as X-direction), and a pair of conveyor supporting units 16A, 16B for fixing and supporting each conveyor unit 15A, 15B. The conveyors 15A, 15B accept the substrate 10 from an upstream mechanism (not shown), carry the substrate 10 to a position contacting a stopper (not shown) arranged on the conveyor 15A or the conveyor 15B and then stop. The stopper is arranged in a projecting manner with respect to a conveyance path of the substrate 10, and rises to fix the substrate at the time of carrying-in of the substrate 10 and lowers when the examination is finished. The conveyors 15A, 15B carry out the substrate 10 to the outside according to the lowering of the stopper.

The conveyor supporting units 16A, 16B are drive-controlled by a substrate control mechanism 78 while supporting each conveyor unit 15A, 15B so as to be movably supported in the X-direction and a Y-direction in FIG. 1. The substrate 10 horizontally moves (moves on a horizontal virtual plane) by the movement of the conveyor supporting units 16A, 16B.

The detector stage 4 includes a pair of slide rails 41A, 41B (hereinafter referred to as "Y-axis rails 41A, 41B") along the Y-axis direction and a slide rail 42 along the X-axis direction (hereinafter referred to as "X-axis rail 42"). Each Y-axis rail 41A, 41B includes a pair of sliders 43. The X-axis rail 42 is supported by having both ends coupled by the slider 43, 43 of each Y-axis rail 41A, 41B.

The X-axis rail 42 includes a large slider 45. A flat panel detector 3 (hereinafter abbreviated as "FPD 3") is attached to the slider 45 through a connection member 46 as a two-dimensional X-ray detector.

The examination apparatus includes a CCD camera 5 and a displacement sensor 6 for detecting a position in the XY plane of the substrate 10 and a position in a height direction perpendicular to the XY plane. A detection output of the CCD (Charge Coupled Device) camera 5 is processed by an image processing mechanism 77B, and a detection output of the displacement sensor 6 is processed by a displacement gauge control mechanism 77A.

The sliders 43, 45 move the FPD 3 when a drive motor (not shown) is drive-controlled by a detector control mechanism 75. Specifically, the FPD 3 moves along the X-axis direction according to the movement of the slider 45, and moves along the Y-axis direction according to the movement of the slider 43 of the Y-axis rails 41A, 41B.

The FPD 3 is connected to the control device 7 through a cable (not shown). The X-ray source 2, the CCD camera 5, the displacement sensor 6, and the drive unit of each stage 1, 4 are also similarly connected with cable to the control device 7.

The CCD camera 5 and the displacement sensor 6 are used for the purpose of checking the state of the substrate 10 before the examination. Specifically, the CCD camera 5 images a fiduciary mark 19 of the substrate 10 to align the substrate 10 to an accurate position. The image imaged by such imaging is input to the image processing mechanism 77B of the control device 7 and used for the measurement of the position shift amount of the substrate 10, and the positional relationship of each stage 1, 4 is adjusted based on the measurement value.

The displacement sensor 6 measures a distance to the upper surface of the substrate 10. The measured distance data is input to the displacement gauge control mechanism 77A of the control device 7, and used for the adjustment of the height of the reference plane T, to be hereinafter described, in the X-ray fluorography.

FIG. 1 shows a block diagram of the main portions of the control device 7 of the examination apparatus of the present embodiment.

The control device 7 executes control related to the X-ray fluorography, and executes the reconstruction process and the examination of the tomographic image. The control device 7 is constructed by a personal computer installed with a dedicated program, and the like. The program may be installed in a main storage unit 71 of the control device 7 at the time of shipment, may be recorded in a recording medium removable with respect to the control device 7 and appropriately installed to the control device 7, or may be downloaded to the control device 7 through the network from a server on the Internet.

The control device 7 includes a calculation unit 70 including a CPU (Central Processing Unit), an auxiliary storage unit 72 including an auxiliary storage device, an input unit 73, including a keyboard, an operation button and the like, for externally accepting input of information, an output unit 74 for outputting image information, audio, and the like, and an X-ray source control mechanism 79 for controlling the X-ray output operation, and the like of the X-ray source 2.

The calculation unit 70 controls the operation of each mechanism such as the detector control mechanism 75, and the like to execute the X-ray fluorography (projection) with respect to the substrate 10 while variously changing a positional relationship of the X-ray source 2, the FPD 3, and the substrate 10. The calculation unit 70 also has a function of controlling the operations of the CCD camera 5, the displacement sensor 6, and the conveyor units 15A, 15B, a function of performing positional adjustment of the substrate 10 based on the input from the CCD camera 5, and a function of changing the set value of the height of the reference plane T at the time of photographing based on the input from the displacement sensor 6 and adjusting the movement amount of the substrate 10 and the FPD 3 in accordance with such change.

In the examination apparatus, the X-ray fluorography is performed over a plurality of times while changing a position of the FPD 3 for every examination region for a plurality of examination regions of the substrate 10, as hereinafter described. The X-ray perspective image generated by the X-ray fluorography of every time is stored in the auxiliary storage unit 72. The calculation unit 70 sets information for identifying the corresponding examination region and the position of the FPD 3 at the time of photographing as additional information to the images, and saves such additional information in the auxiliary storage unit 72 in correspondence with the images. The calculation unit 70 determines the appropriateness of the site to be examined of the substrate 10 based on the data obtained by reconstruction. The determination result is output to the output unit 74 such as a monitor, the external device, and the like.

[2. Tomosynthesis Photographing and Reconstruction Process]

Figure 2:
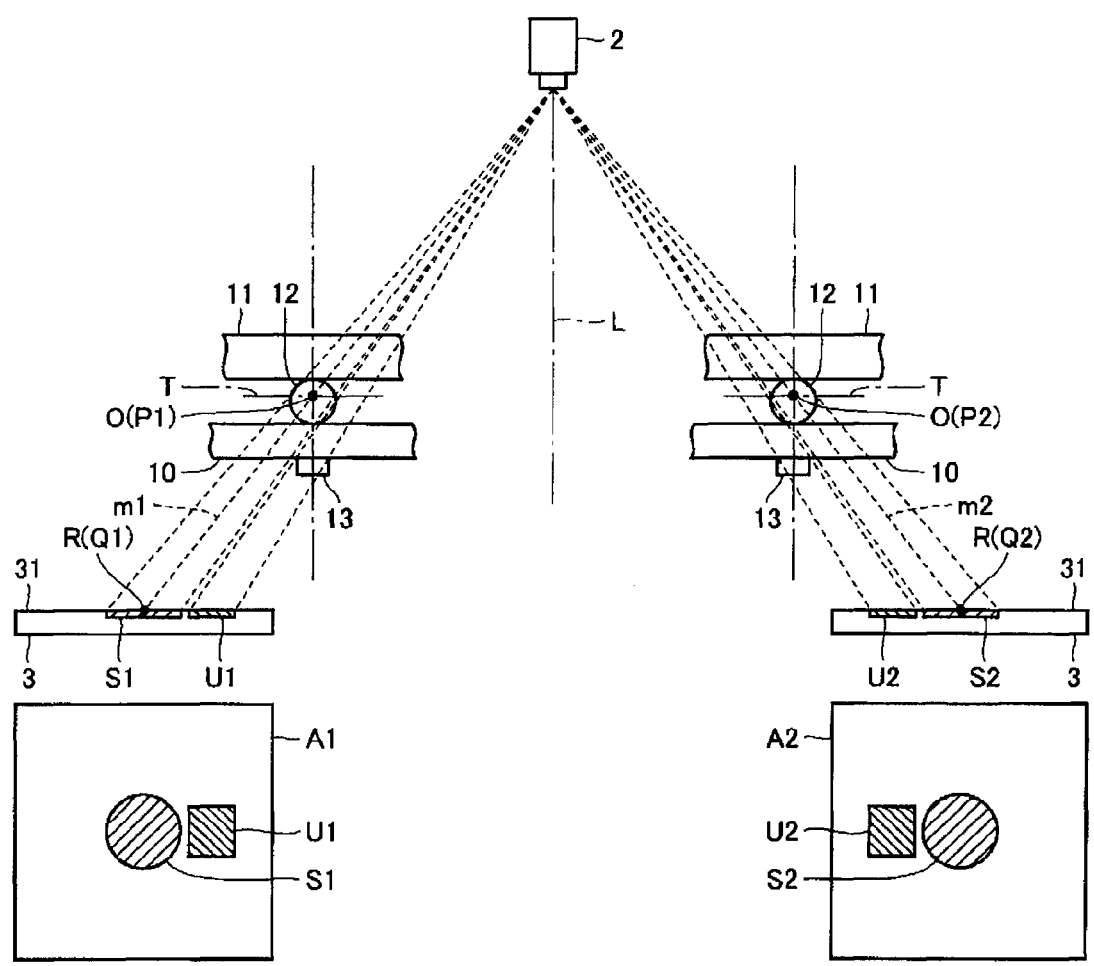
FIG. 2 is a view schematically showing a positional relationship of an X-ray source, a FPD, and a substrate when photographing an X-ray perspective image in the examination apparatus of FIG. 1.

FIG. 2 is a view schematically showing a positional relationship of the X-ray source 2, the FPD 3, and the substrate 10, when performing the tomosynthesis photographing. In FIG. 2, one part of the substrate 10 is shown in an enlarged manner. In FIG. 2, a solder electrode 12 for connecting the component 11 is shown on the substrate 10, and a component 13 (hereinafter referred to as "back surface component 13") mounted on the back surface side of the substrate 10 is shown. In FIG. 2, a plane T serving as a plane transversing the three-dimensional examination region including the solder electrode 12 along the horizontal direction is shown. The plane T is used as a reference in fluorography. Point O is a reference point set at a predetermined position of the plane T.

In the tomosynthesis photographing, the substrate 10 is moved so that the reference point O is aligned with two points P1, P2, which are positions of point symmetric with the optical axis L of the X-ray source 2 as a reference, and the FPD 3 is moved to a position (points Q1, Q2 in FIG. 2) where the positioned reference point O is projected to a center point R of a detection surface 31 of the FPD 3, and photographing is carried out at such positions. Since a conical beam is emitted from the X-ray source 2, the irradiation angle of the X-ray with respect to the reference point O at each position is substantially the same. Furthermore, distances with respect to the optical axis L of the points Q1, Q2 where the center point R of the detection surface 31 is aligned are equal since distances of the points P1, P2 with respect to the optical axis L are equal. Therefore, each point in the plane T including the reference point O is projected to the same coordinate of the detection surface 31 in both photographing at the positions Q1 and Q2. The point in the examination region at a height different from the plane T such as the constructing point of the back surface component 13, on the other hand, is projected to different positions in the detection surface 31 every time a photographing position changes.

Figure 3:
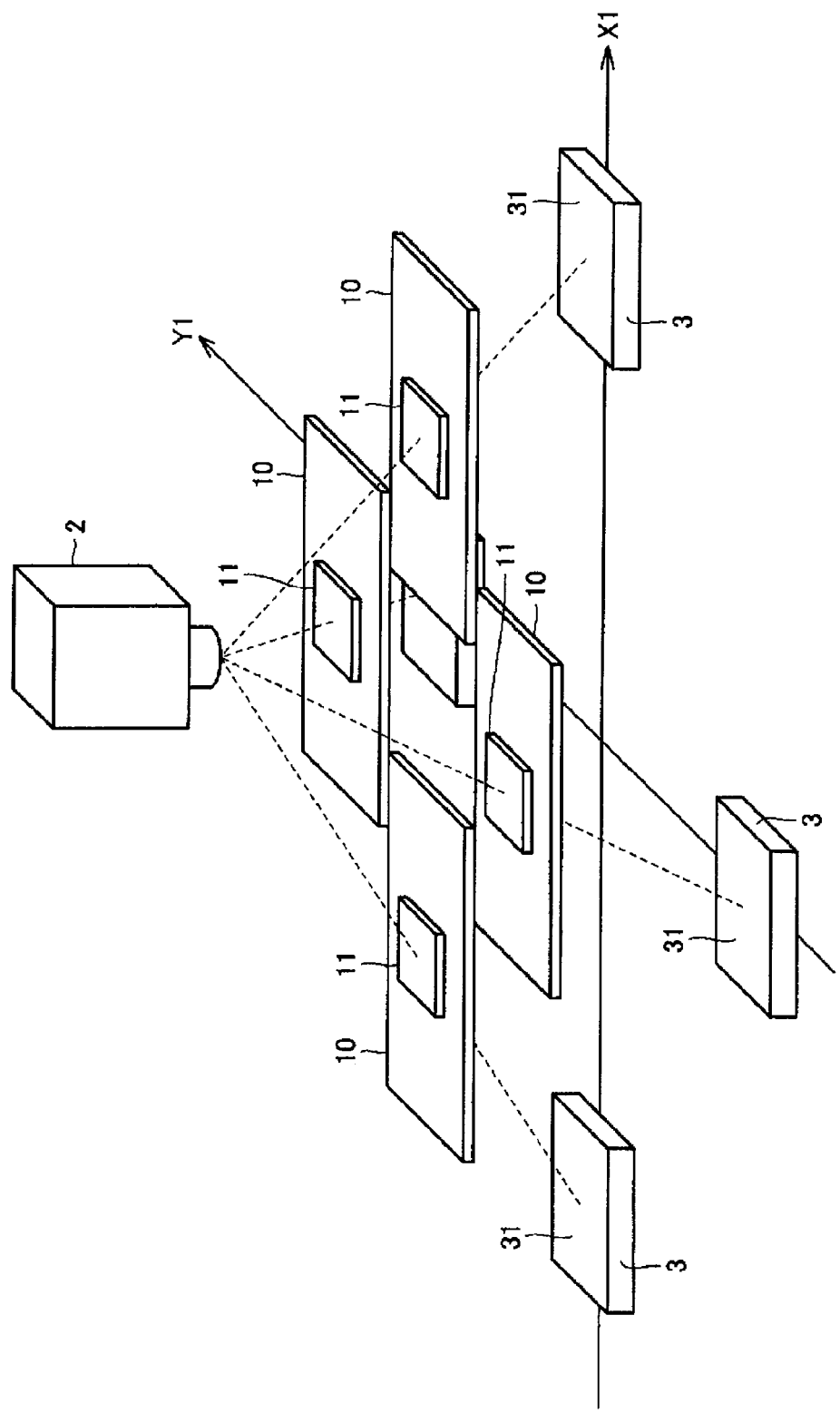
FIG. 3 is a view showing one example of change in positions of the substrate and the FPD in a photographing process for one cycle in the examination apparatus of FIG. 1.

Based on the above principle, in the present embodiment, a plurality of combinations of the orientations in an opposing relationship through the optical axis of the X-ray source 2 is selected, as shown in FIG. 3, and the calculation unit 70 controls the operation of each control mechanism (substrate control mechanism 78, detector control mechanism 75) of the substrate stage 1 and the detector stage 4 so that the X-ray source 2, the FPD 3, and the substrate 10 stop with a positional relationship similar to that shown in FIG. 2 in such orientations. X1, Y1 in FIG. 3 are drive axes of the detector stage 4, and are set in directions parallel to the drive axis of the substrate stage 1 (not shown), that is, an end edge direction in each direction of the substrate 10. The direction of each coordinate axis of the coordinate system of the two-dimensional image of the FPD 3 in this case is also aligned with X1, Y1.

Figure 4:
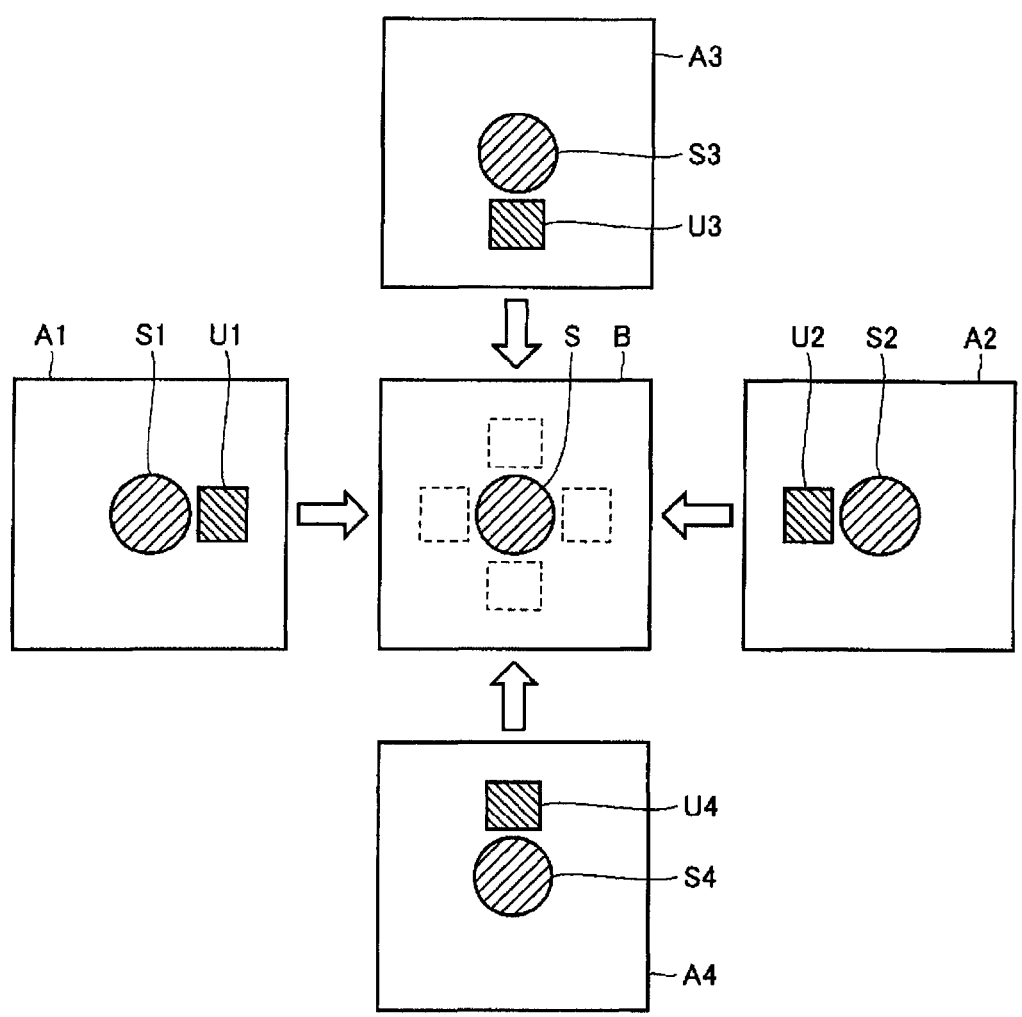
FIG. 4 is a view describing a principle of the reconstruction process of the tomographic image through tomosynthesis in the examination apparatus of FIG. 1.

In FIG. 4, the X-ray perspective images A1, A2, A3, which are generated by positioning the substrate 10 and the FPD 3 in four orientations shown in FIG. 3 and performing photographing, are arranged in correspondence with the orientation of the FPD 3 at the time of photographing, and the tomographic image B in the data obtained by reconstructing each image is arranged at the middle of such images. Each image shows the site with high X-ray absorptivity (correspond to site with high tone in image data) with a shaded pattern for the sake of convenience of the illustration.

S1 to S4 in each image A1 to A4 are projection ranges of the solder electrode 12, and U1 to U4 are projection ranges of the back surface component 13. As described with reference to FIG. 2, the constructing point of the solder electrode 12 in the plane T is projected to the same coordinate in all X-ray perspective images A1 to A4, but the coordinate to which the constructing point of the back surface component 13 is projected moves depending on the image.

In the present embodiment, the data of the pixel indicating the lowest X-ray absorptivity in a set is selected for every set of pixels in a correspondence relationship between the images, and the tomographic image B is generated by each selected data, focusing on the above aspect in generating the reconstruction data through tomosynthesis.

When reconstructing the tomographic image of a plurality of planes to obtain three-dimensional data of the examination region, the coordinate of the constructing point of the target plane in the image is made the same by shift correcting each X-ray perspective image based on the ratio of the height with respect to the reference plane for each plane, and a method shown in FIG. 4 is applied.

According to the generation of the reconstruction data through tomosynthesis, data representing the solder electrode 12 is selected regardless of the image data selected for the pixels corresponding to the projection ranges S1 to S4 of the solder electrode 12. On the other hand, the image data (image data with smallest noise component) in which the back surface component 13 is not projected is selected for the areas other than the projection range of the solder electrode 12, and thus the image of the back surface component 13 does not appear in the tomographic image B.

Figure 5:
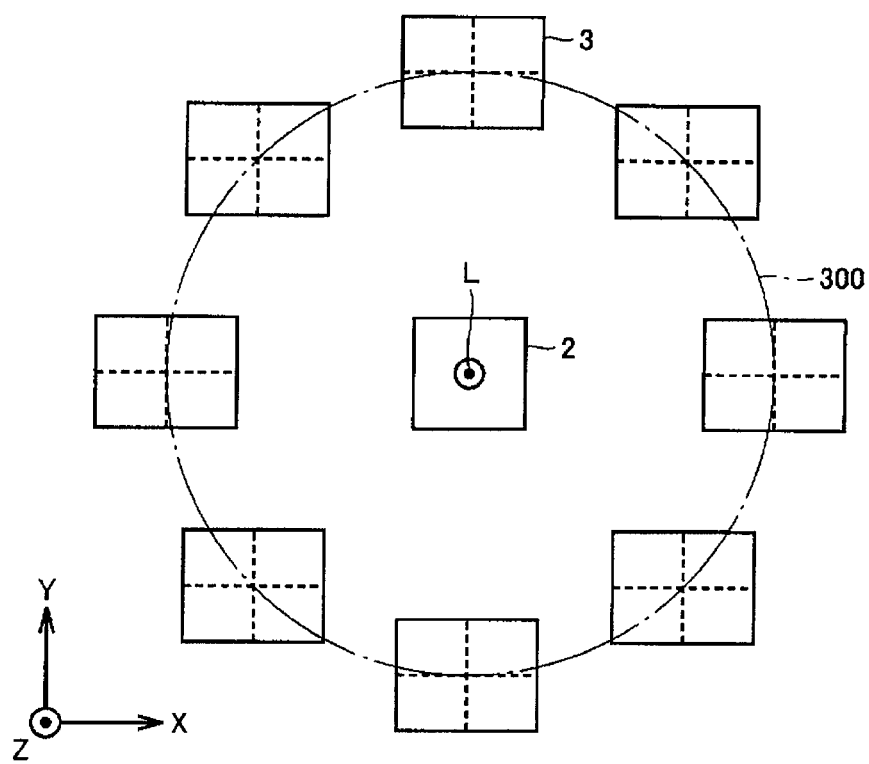
FIG. 5 is a view schematically showing change in positional relationship between the X-ray source and the FPD in the photographing process in the examination apparatus of FIG. 1.

FIG. 5 schematically shows change in a positional relationship between the X-ray source 2 and the FPD 3 (detection region thereof) when performing the tomosynthesis photographing.

In the example shown in FIG. 5, the FPD 3 is stopped and the photographing is performed at eight orientations, which are the four orientations shown in FIG. 3 and the four orientations intermediate of such orientations shown in FIG. 3.

As previously described, the distance between the FPD 3 and the optical axis L of the X-ray source 2 at the time of photographing is always constant, and thus the FPD 3 in the photographing of every time is assumed to be positioned on a virtual circle 300 having the optical axis L as the center. In this example, the operation of the detector stage 4 is controlled such that the FPD3 moves in turn to positions corresponding to the eight orientations along the virtual circle 300 (i.e., changing the orientation of the FPD 3 by 45° with the optical axis L as the center), and temporarily stops at each position. Although the illustration is omitted in FIG. 5, the operation of the substrate 1 is similarly controlled such that the substrate 10 moves along a virtual circle having the optical axis L of the X-ray source 2 as the center, and stops at a position the relationship shown in FIG. 2 is always satisfied when the FPD is stopped. The substrate 10 and the FPD 3 can be linearly moved and efficiently moved by adjusting the movement amount in the X, Y-directions of the substrate stage 1 and the detector stage 4.

[3. X-ray CT Photographing]

In the present embodiment, the positional relationship between the X-ray source 2 and the FPD 3 in a case of performing the X-ray CT photographing is similar to a case of performing the tomosynthesis photographing. That is, in the X-ray CT photographing as well, the position of the FPD 3 moves in turn along the virtual circle having the optical axis of the X-ray source 2 as the center, but does not rotate with the center of the detection region as the axis, as described with reference to FIG. 20A when photographing is performed over a plurality of times with respect to one examination region of the substrate 10.

In the present embodiment, the FPD 3 is linearly moved by a predetermined angle along the virtual circle 300 having the optical axis L of the X-ray source 2 as the center in the X-ray CT photographing as well, similar to the tomosynthesis photographing. With respect to the substrate 10 as well, the operation of the substrate stage 1 is controlled such that a relationship in which the reference point O is projected to the center point R of the imaging plane 31 is maintained in all photographing with one point in the plane T having a predetermined height as the reference point O, similar to the tomosynthesis photographing.

[4. Reconstruction Process by X-Ray CT]

A specific example of a reconstruction data generating mode by the X-ray CT in the examination apparatus of the present embodiment will be described.

4-1. Example of First Reconstruction Data Generating Mode

In the examination apparatus of the present embodiment, when the X-ray fluorography is performed, distortion that arises when a normal direction of the detection surface 31 of the FPD 3 does not match the center line of the X-ray transmitted through the substrate is first corrected for the images generated by photographing of every time, and the corrected image is converted to an image showing a state seen from a direction orthogonal to the thickness of the substrate 10. Furthermore, conversion to the absorption coefficient data is carried out by calculating the X-ray absorptivity of each constructing point of the plane to be processed using each image obtained after the conversion, filtering process is performed on the absorption coefficient data, and then the pixel value of the absorption coefficient data for each reconstructing pixel in all projection data generated by photographing is added for every pixel (reconstructing pixel) constructing the reconstruction data.

In the first example, the FPD 3 is moved on the virtual circle having the optical axis of the X-ray source 2 as the center, the obtained X-ray perspective image is rotated with the center of the image as an axis according to the rotation angle on the virtual circle for a plurality of X-ray perspective images obtained at each of a plurality of positions to which the FPD 3 is moved, and then the filtering process is performed.

This will be more specifically described with reference to FIGS. 6A and 6B and FIG. 7.

Figure 6A:
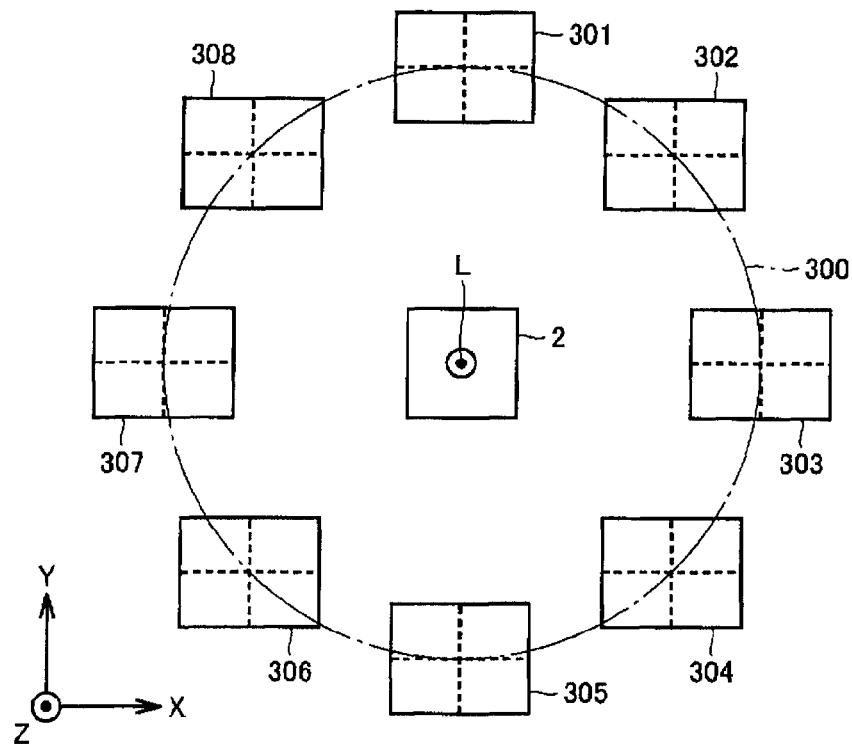
FIGS. 6A and 6B are views describing change in arrangement due to rotation of the image data in generation of the reconstruction data through the X-ray CT in the examination apparatus of FIG. 1.
Figure 20A:
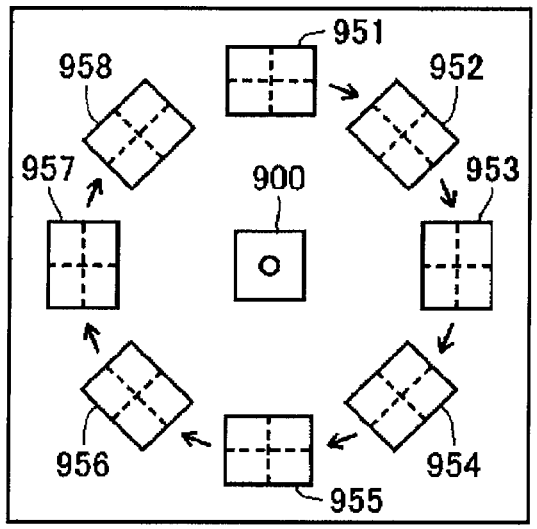
FIGS. 20A to 20C are views describing the problems anticipated when performing the X-ray CT photographing and the tomosynthesis photographing in the conventional examination apparatus.
Figure 20B:
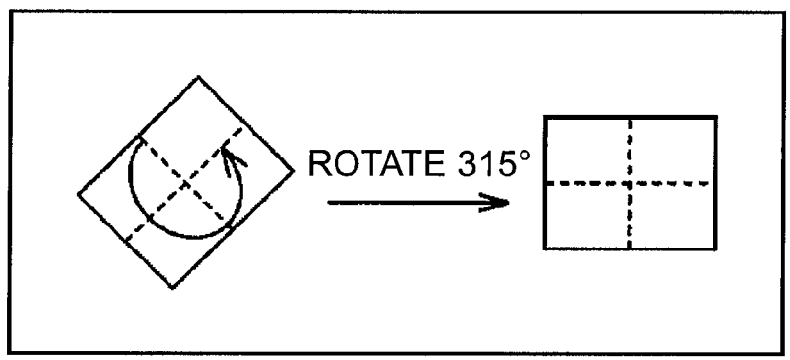
Figure 20C:
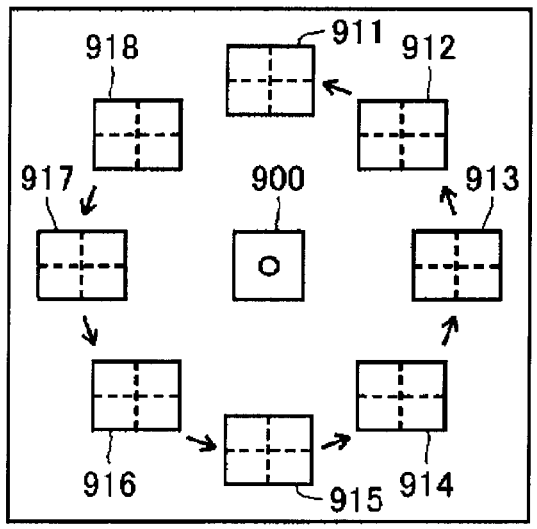

FIG. 6A shows positions 301 to 308 of the FPD 3 on the virtual circle 300 having the optical axis L of the X-ray source 2 as the axis. In the examination apparatus of the present embodiment, the X-ray perspective images are photographed at the plurality of positions 301 to 308 on the same virtual circle 300 even in the photographing for generating the three-dimensional image through the X-ray CT, similar to the photographing for generating the tomographic image through the tomosynthesis. That is, even when the FPD 3 is moved on the virtual circle 300 in the photographing for generating the three-dimensional image through the X-ray CT, the FPD 3 is not controlled so as to rotate with the center thereof as the axis as shown in FIG. 20A.

Figure 6B:
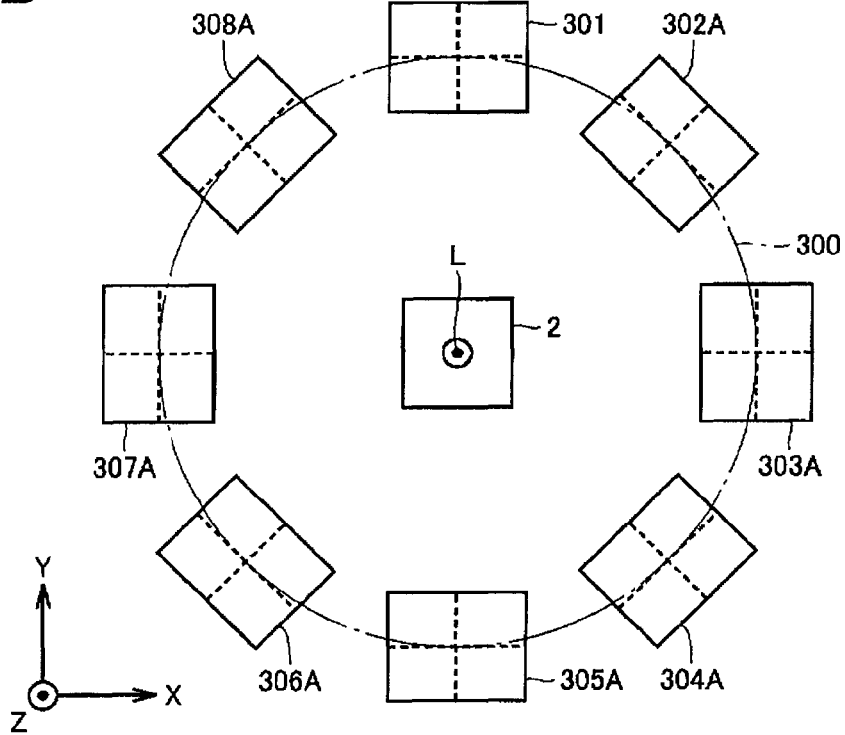

In this example, data is converted so that each image rotates using affine conversion with the center of each X-ray perspective image as the axis according to a rotation position on the virtual circle 300 as if the X-ray perspective images obtained at each position 302 to 308 in FIG. 6A are photographed at positions 302A to 308A shown in FIG. 6B. In this example, the image obtained at position 302 is assumed as the image photographed at the position 302A by being rotated 45° with the center thereof as the axis, the image obtained at position 303 is assumed as the image photographed at the position 303A by being similarly rotated 90°, the image obtained at position 304 is assumed as the image photographed at the position 304A by being similarly rotated 135°, the image obtained at position 305 is assumed as the image photographed at the position 305A by being similarly rotated 180°, the image obtained at position 306 is assumed as the image photographed at the position 306A by being similarly rotated 225°, the image obtained at position 307 is assumed as the image photographed at the position 307A by being similarly rotated 270°, and the image obtained at position 308 is assumed as the image photographed at the position 308A by being similarly rotated 315°.

Figure 7:
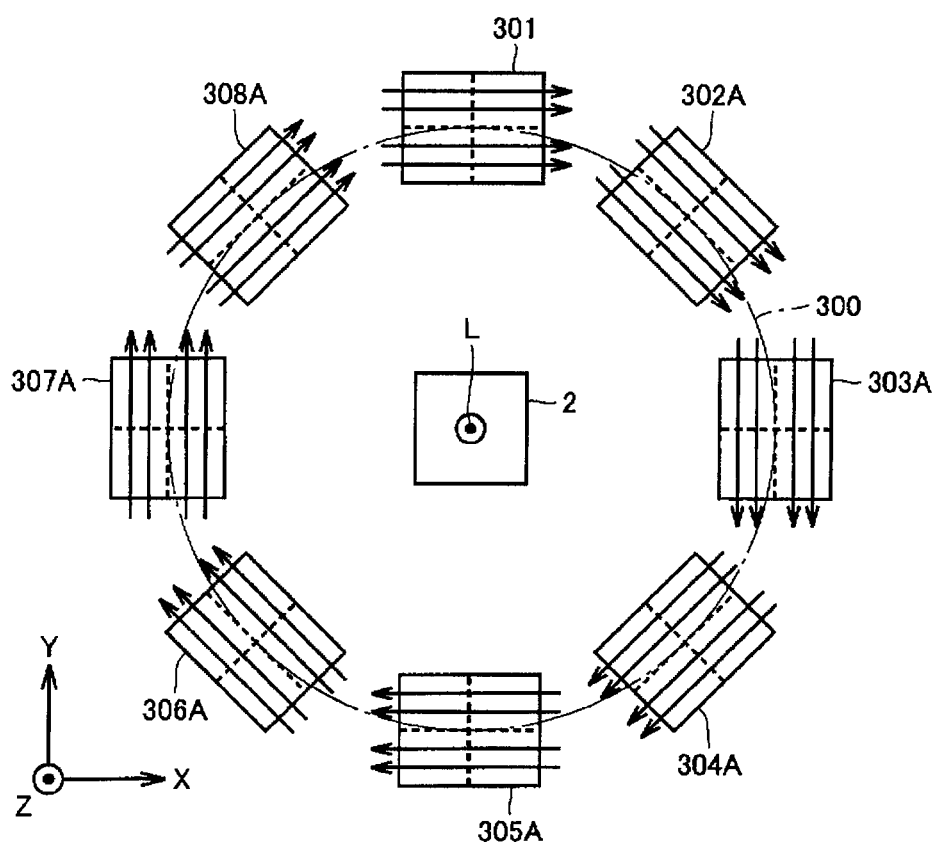
FIG. 7 is a view describing the direction of the filtering process in the generation of the reconstruction data through the X-ray CT in the examination apparatus of FIG. 1.

The filtering process is performed on the rotation processed image, as shown in FIG. 7, the reconstructing pixels are acquired based on the data subjected to the filtering process, and the reconstruction data is acquired therefrom.

In FIG. 7, the arrow shown with the position 301 and the positions 302A to 308A schematically shows the direction of the filtering process on the image photographed at each position. In each image, the direction of the filtering process is set in the direction along a longitudinal direction of the outer line represented with a rectangle.

Therefore, the direction of the image of each examination region with respect to the substrate 10 may be set similar to FIG. 20A without rotating the detection region of the two-dimensional X-ray detector with the center thereof as the axis (see FIG. 20A) as in the prior art when moving the detection region on the virtual circle by performing the filtering process after performing data conversion so that the image rotates.

Therefore, according to this example, the data of the three-dimensional image by the X-ray CT image can be generated using the reconstruction algorithm of the X-ray CT image adopted in the conventional examination apparatus, which includes a mechanism of rotating the FPD 3 with the center of the detection region thereof as the axis, without including such mechanism.

4-2. Example of Second Reconstruction Data Generating Mode

Figure 8:
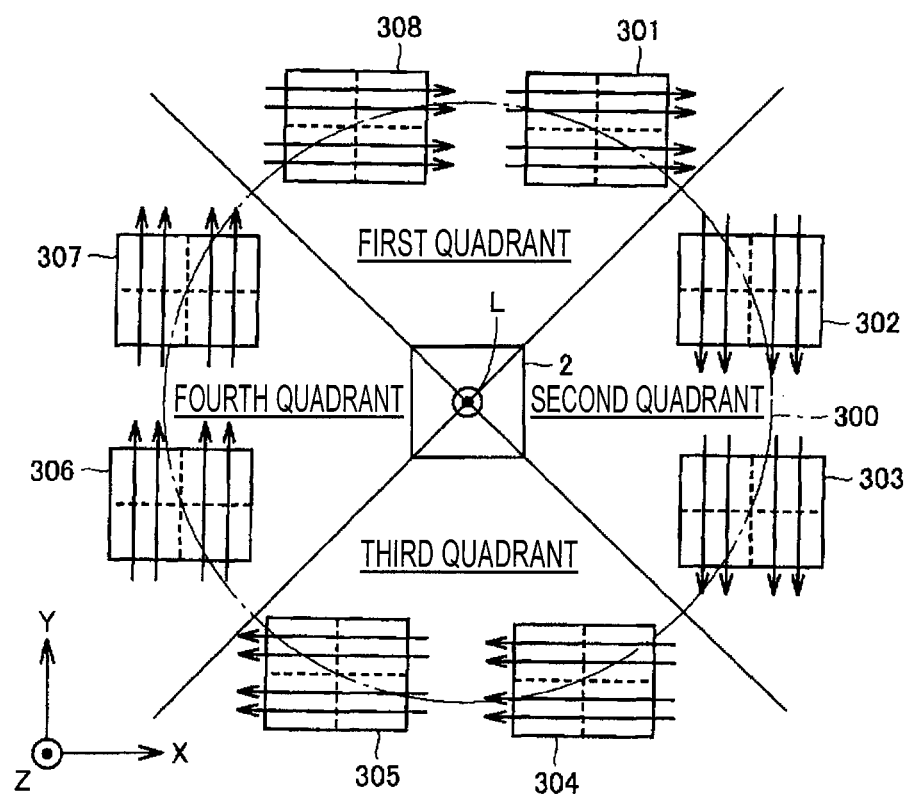
FIG. 8 is a view describing the direction of the filtering process in the generation of the reconstruction data through the X-ray CT in the examination apparatus of FIG. 1.

In this example, the direction of the filtering process with respect to the X-ray perspective image is set as shown in FIG. 8.

With reference to FIG. 8, the range is set for a rotation position on the virtual circle 300 at the positions 301 to 308 on the virtual circle 300, and the direction of the filtering process is set for every range. Specifically, the direction of the filtering process is set for every rotation position of 90°.

In the example shown in FIG. 8, the photographing of the X-ray perspective image is performed for every rotation position 45° on the virtual circle 300. The direction of the filtering process is set for every rotation position 90°. That is, if the optical axis L of the X-ray source 2 is the origin of the XY plane, the image photographed at the positions 308, 301, in which the center is in a first quadrant, has the direction of the filtering process set in the direction from the left to the right in the horizontal direction; the image photographed at the positions 302, 303, in which the center is in a second quadrant, has the direction of the filtering process set downward in the Y-axis direction, the image photographed at the positions 304, 305, in which the center is in a third quadrant, has the direction of the filtering process set in the direction from the right to the left in the X-axis direction; and the image photographed at the positions 306, 307, in which the center is in a fourth quadrant, has the direction of the filtering process set from the bottom to the top in the Y-axis direction.

4-3. Example of Third Reconstruction Data Generating Mode

Figure 9:
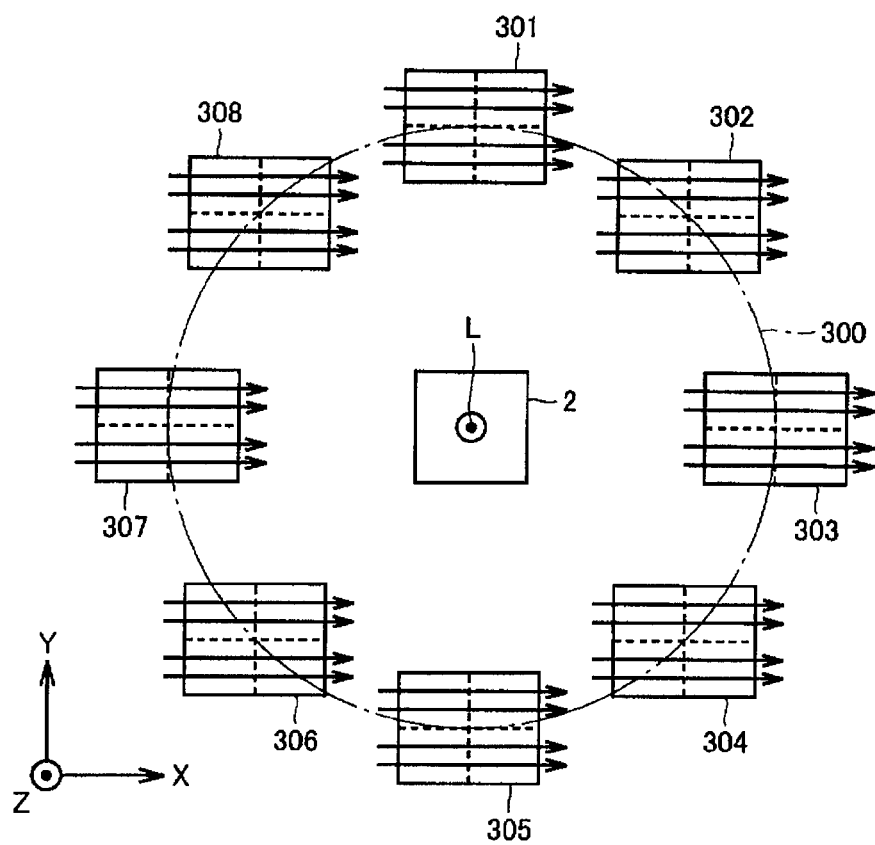
FIG. 9 is a view describing the direction of the filtering process in the generation of the reconstruction data through the X-ray CT in the examination apparatus of FIG. 1.

The direction of the filtering process with respect to the X-ray perspective image maybe set from the left to the right along the X-axis with respect to the positions 301 to 308 on the virtual circle 300, as shown in FIG. 9.

Thus, the filtering process is performed in the longitudinal direction of a rectangle, which is the detection region, for all the X-ray perspective images. Therefore, the process can be performed at the highest speed with respect to the data arranged in a matrix form within the rectangular shape.

The filter used in the present embodiment is a high frequency accentuation filter, and thus the image quality is not influenced in terms of performing examination of the solder electrode and the like of the substrate 10 even if the direction of the filtering process with respect to the substrate 10, which is the examination target, is different among the X-ray perspective images photographed at different positions, as shown in FIG. 9.

4-4. Example of Fourth Reconstruction Data Generating Mode

Figure 10A:
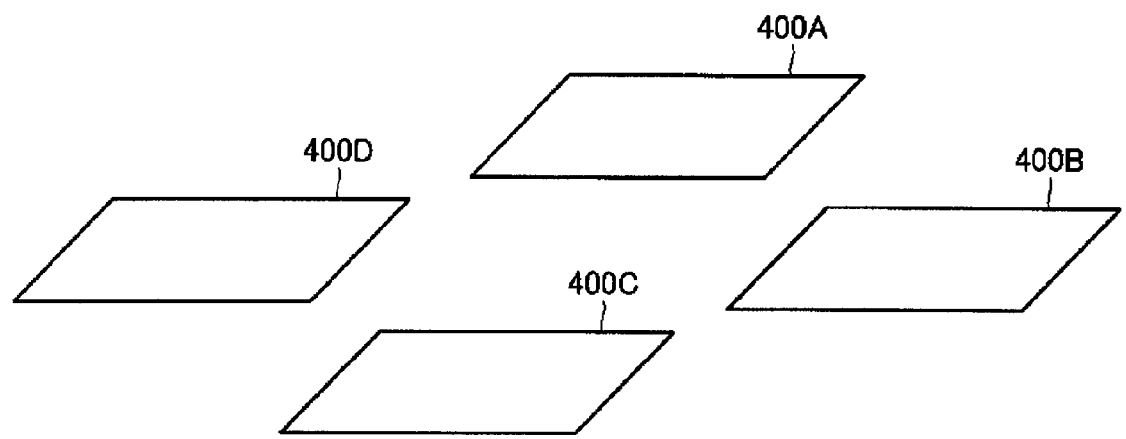
FIGS. 10A to 10C are views describing one example of a reconstruction data generating mode by the X-ray CT in the examination apparatus of FIG. 1.
Figure 10B:
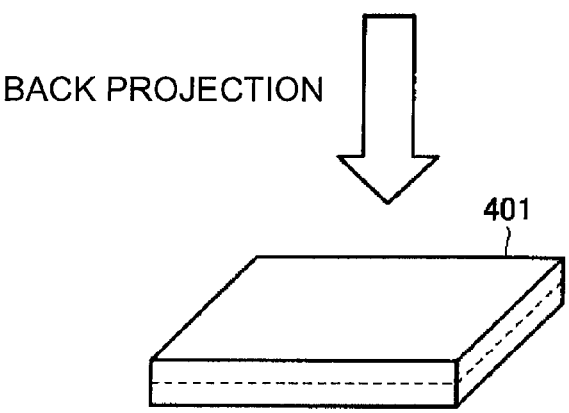

In this example, when the X-ray perspective image is photographed at a plurality of positions on the virtual circle, as shown as the virtual circle 300, as shown in 400A to 400D in FIG. 10A, a temporary three-dimensional image 401 is first generated, as shown in FIG. 10B, by back projecting the images, the data constructing the obtained three-dimensional image 401 is sliced at a predetermined interval to obtain a cross-section perpendicular to the optical axis of the X-ray source, as shown with a broken line in FIG. 10B, and the filtering process is performed for two directions intersecting each other, as shown with four arrows each for each direction in FIG. 10O with respect to the image data on the obtained cross-section 402, as shown in FIG. 10O. The final three-dimensional image data can be obtained by again stacking the image data of each cross-section subjected to the filtering process.

The predetermined interval in obtaining the slice image of the cross-section from the three-dimensional image 401 shown in FIG. 10B preferably takes into consideration the size of the element that becomes a target of examination such as the solder electrode constructing the back fillet or the BGA formed on the lead of the IC. Specifically, the predetermined interval is preferably a minimum value of the assumed ball size when performing the examination on the solder electrode of the BGA.

The direction of the filtering process of two types is preferably directions respectively parallel to the two adjacent sides if the cross-sectional shape of the three-dimensional image 401 is a rectangle as shown in FIG. 10O.

As described in the examples of the first to the third reconstruction data generating modes, the direction of the filtering process at each cross-section my not be two types vertically and horizontally as shown in FIG. 10O, and may be a single direction in this example as well. Although the processing time becomes long if the direction of the filtering process is in plurals, the three-dimensional image of the examining object can be more accurately obtained.

[5. Substrate Examination Process]

The content of the substrate examination process executed in the examination apparatus of the present embodiment will now be described. In the examination apparatus, the respective three-dimensional image data can be reconstructed for a plurality of examination regions with respect to the substrate 10 to be examined.

5-1. Specific Example of Substrate Examination Process

FIG. 11 is a flowchart of one example of the substrate examination process executed by the calculation unit 70.

With reference to FIG. 11, when information notifying to start the examination of the substrate is input to the input unit 73, and the like, the calculation unit 70 moves the FPD 3 to a position of photographing the X-ray image of the first field of view of a plurality of field of views, which is the examination target of the substrate 10, in step S10, and proceeds the process to step S20.

In step S20, the calculation unit 70 performs the photographing (projection) at a first position of a plurality of photographing positions on the virtual circle 300 at the photographing position at the relevant time point, as shown in FIG. 6A, and proceeds the process to step S30.

In step S30, the substrate stage 1 and the detector stage 4 are moved for the photographing (projection) at a next position on the virtual circle 300 at the relevant time point, and proceeds the process to step S40.

In step S40, the calculation unit 70 performs the photographing (production) at a position the stages are moved in step S30 immediately before step S40, and proceeds the process to step S50.

In step S50, the calculation unit 70 accepts the image data obtained in the photographing of step S40 immediately before step S50 from the FPD 3 through the image acquiring mechanism 76, saves the image data in the auxiliary storage unit 72, and proceeds the process to step S60.

In step S60, whether or not the photographing of a set number defined in advance to generate the three-dimensional image data currently being generated is finished is determined, where the process proceeds to step S70 if determined as finished and the process returns to step S30 if determined as not yet finished.

Therefore, the FPD 3 and the substrate 10 are moved at the photographing position moved in step S10, and the photographing of a plurality of X-ray perspective images necessary to generate one three-dimensional image is performed as in the images A1 to A4 of FIG. 4 and the X-ray perspective images 301 to 308 of FIG. 6A.

The calculation unit 70 completes the projection photographing at the photographing position of the relevant time point of the three-dimensional image to be generated in step S70, and proceeds the process to step S80.

In step S80, the calculation unit 70 accepts the input of information for selecting whether to have the reconstruction data generated as an image to be used in the examination of the substrate 10 as the X-ray CT image or the image of tomosynthesis, and proceeds the process to step S90.

In step S80, the calculation unit 70 may display the information urging the input of the information on selecting either image on the output unit 74.

In step S90, whether or not the result of the information accepted in step S80 is the image of the X-ray CT is determined, where the process proceeds to step S100 if determined as the image of the X-ray CT and the process proceeds to step S110 if determined as not the image of the X-ray CT, that is, determined as the image of tomosynthesis.

In step S100, the calculation unit 70 executes a process of generating the data of the reconstructing pixel for generating the reconstruction data by the X-ray CT, and proceeds the process to step S120.

In step S110, the calculation unit 70 executes a process of generating the data of the reconstructing pixel for generating the reconstruction data by the tomosynthesis, and proceeds the process to step S120.

In step S120, the calculation unit 70 generates the reconstruction data using the data of the reconstructing pixel generated in step S100 or step S110, and proceeds the process to step S130.

In step S130, the calculation unit 70 executes the examination (determination on quality of solder electrode etc.) on the examination region with respect to the reconstruction data based on the reconstruction data generated in step S120, and proceeds the process to step S140.

In step S140, the calculation unit 70 determines whether or not the examination on all examination regions is finished with respect to the substrate 10, which is the examination target. If determined as not yet finished, steps S10 to S130 are executed for the next examination region. If determined as finished, the substrate examination process on the substrate 10, which is the examination target, is terminated.

5-2. Generation of Reconstructing Pixel for Generating Reconstruction Data by Tomosynthesis FIG. 12 is a flowchart of a sub-routine of the process of generating the reconstructing pixel for generating the reconstruction data by tomosynthesis of step S110.

Figure 12:
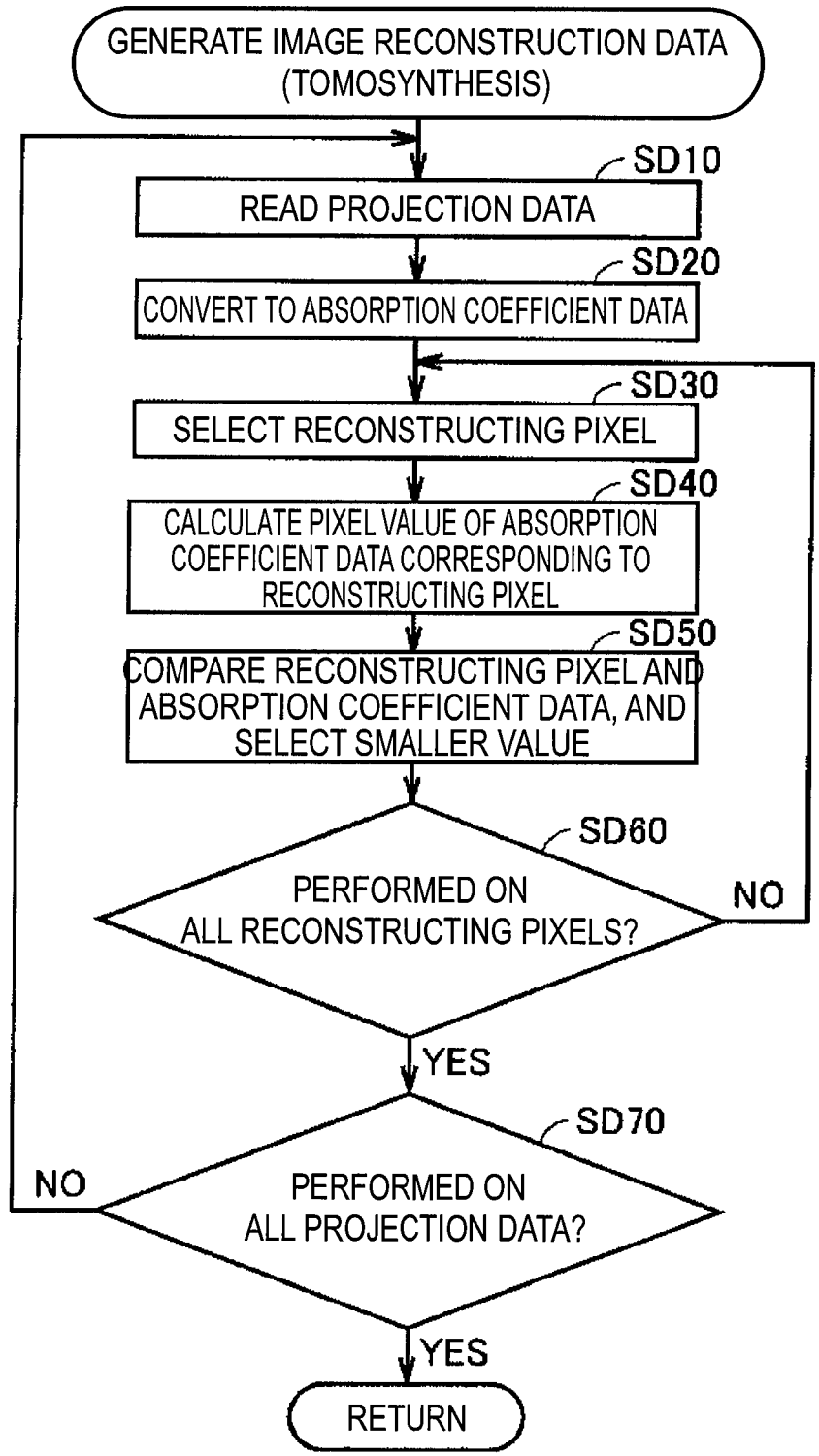
FIG. 12 is a flowchart of a sub-routine of step S110 of FIG. 11.

With reference to FIG. 12, in the relevant process, the calculation unit 70 first reads the projection data stored in the auxiliary storage unit 72 in step SD10, and proceeds the process to step SD20.

The projection data read here is the image data for one time of the image data obtained through the photographing of plural times by the FPD 3 with respect to a predetermined field of view on the substrate 10, which is the target of generation of the reconstruction data. In the present embodiment, the three-dimensional data is reconstructed by photographing a plurality of X-ray perspective images from different directions for every field of view set for the substrate 10.

In step SD20, the calculation unit 70 converts the data to the absorption coefficient data by calculating the X-ray absorptivity for the data of each pixel of the projection data read in step SD10, and proceeds the process to step SD30.

In step SD30, one reconstructing pixel of the pixels (reconstructing pixels) constructing the reconstruction data is selected, and the process proceeds to step SD40.

In step SD40, the pixel value of the absorption coefficient data for the reconstructing pixel selected in step SD30 immediately before step SD40 is calculated from the projection data read in step SD10, and the process proceeds to step SD50.

In step SD50, the calculation unit 70 compares the pixel value (absorption coefficient data) calculated in step SD40 executed immediately before step SD 50 for the reconstructing pixel serving as the processing target selected in step SD30, and the pixel value (absorption coefficient data) calculated for the reconstructing pixel up to this point, selects the higher pixel value (lower absorption coefficient data), and proceeds the process to step SD60. When step SD50 is executed for the first time for the reconstructing pixel, the pixel value (absorption coefficient data) in step SD40 executed immediately before step SD 50 is selected. In step SD50, either the pixel value or the absorption coefficient data may be selected as the processing target.

In step SD60, whether or not the selection of the data in step SD50 is performed for all reconstructing pixels in the reconstruction data in the projection data read in step SD10 is determined, where the process returns to step SD30 if the reconstructing pixel in which selection is not yet performed exists, and the process proceeds to step SD70 if the selection is performed for all reconstructing pixels.

In step SD70, the calculation unit 70 determines whether or not the process of steps SD10 to SD60 are executed for all the projection data stored in the auxiliary storage unit 72, and returns the process to step SD10 if determined that the projection data in which the processes are not yet executed exists, and returns the process to FIG. 11 if determined that the processes are executed for all projection data.

Through the processes of steps SD10 to SD70 described above, the selection of the pixel value and the like is performed in order to all reconstructing pixels for every one projection data with respect to plural projection data stored in the auxiliary storage unit 72. The data with the highest pixel value (data with smallest absorption coefficient data) of the plural projection data is selected for all reconstructing pixels.

5-3. Generation of Reconstructing Pixel for Generating Reconstruction Data by X-Ray CT (1)

Figure 13:
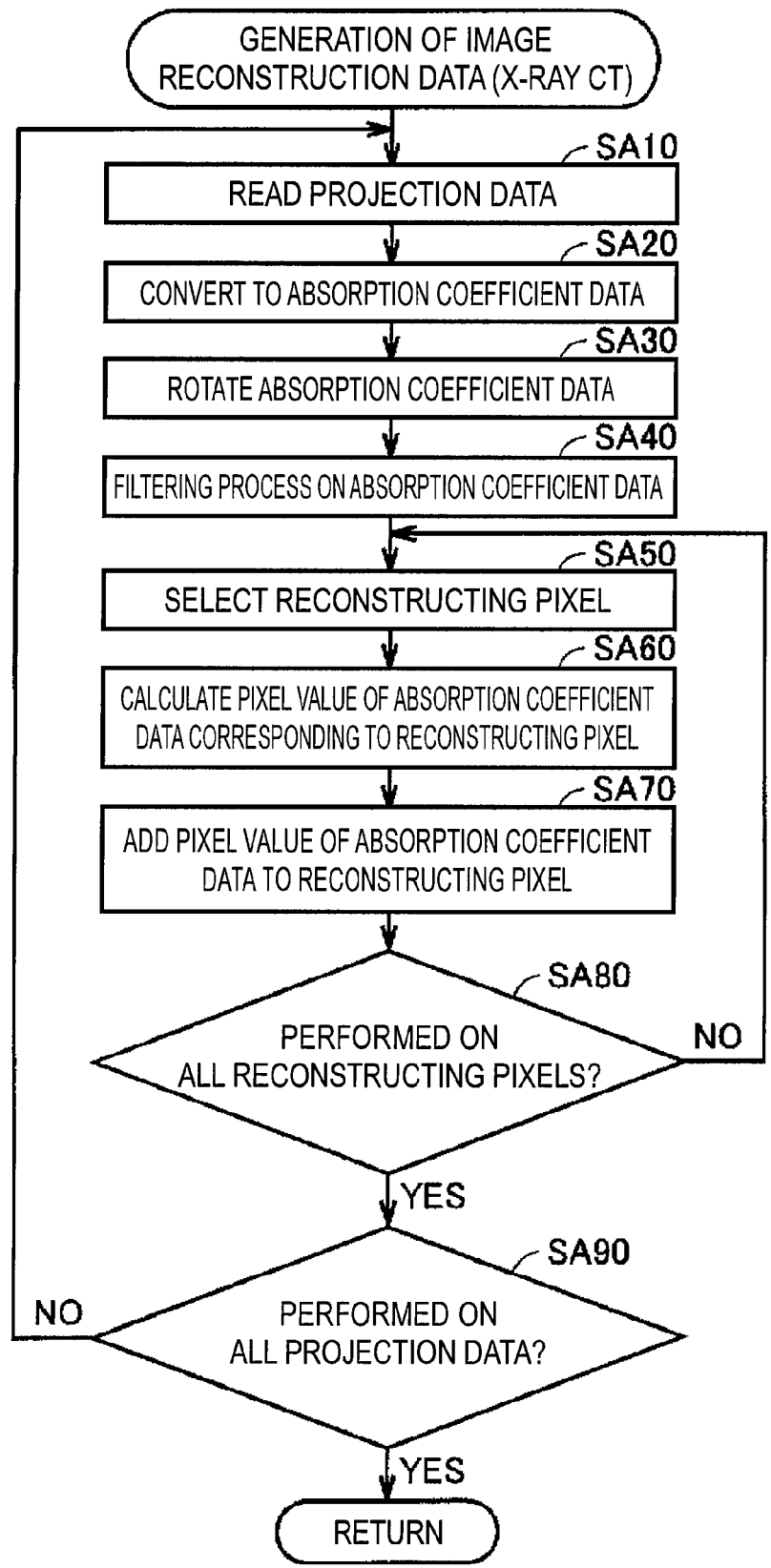
FIG. 13 is a flowchart of a sub-routine of step S100 of FIG. 11.

FIG. 13 is a flowchart of a sub-routine of the process of generating the data of the reconstructing pixel for generating the reconstruction data by the X-ray CT.

With reference to FIG. 13, in the relevant process, the calculation unit 70 first reads the projection data stored in the auxiliary storage unit 72 in step SA10, and proceeds the process to step SA20.

The projection data read here is similar to the projection data read in step SD10 of the process described with reference to FIG. 12. That is, in the examination apparatus of the present embodiment, the projection data for generating the reconstructing pixel for the reconstruction data generation by the X-ray CT can be shared with the projection data for generating the reconstructing pixel for the reconstruction data generation by the tomosynthesis.

In step SA20, the calculation unit 70 converts the image data of each pixel of the projection data read in step SA10 to the absorption coefficient data, similar to step SD20 (see FIG. 12), and proceeds the process to step SA30.

In step SA30, the calculation unit 70 rotatably moves the coordinate of the absorption coefficient data obtained in step SA20 according to a rotating position having the optical axis of the X-ray source 2 as the center for each X-ray perspective image photographed at different positions on the same virtual circle 300, as described with reference to FIGS. 6A and 6B, and proceeds the process to step SA40.

In step SA40, the calculation unit 70 performs the filtering process as shown in FIG. 7 on the absorption coefficient data, in which the coordinate is rotatably moved in step SA30, and proceeds the process to step SA50.

In step SA50, one reconstructing pixel in the reconstruction data is selected, and the process proceeds to step SA60.

In step SA60, the calculation unit 70 calculates the absorption coefficient data and/or pixel value corresponding to the reconstructing pixel selected in step SA50 immediately before step SA60 from the data subjected to the filtering process of step SA40, and proceeds the process to step SA70.

In step SA70, the pixel value calculated in step SA60 immediately before step SA70 is added to the pixel value, added up to this point for the reconstructing pixels selected in step SA50, and the process proceeds to step SA80.

In step SA80, the calculation unit 70 determines whether or not the processes of steps SA50 to SA70 are executed on all reconstructing pixels, and proceeds the process to step SA90 if determined as executed and returns the process to step SA50 if determined that the reconstructing pixel that is not yet the processing target exists.

Through the processes of steps SA50 to SA80, the pixel value is calculated on all reconstructing pixels constructing the reconstruction data with respect to the projection data of the processing target, and the calculated pixel value of each reconstructing pixel is added for every reconstructing pixel.

In step SA90, whether or not the processes of steps SA10 to SA80 are executed on all projection data stored in the auxiliary storage unit 72 is determined, and the process returns to FIG. 11 if determined as executed. If determined that the projection data that is not the processing target exists, the process returns to step SA10, and the processes of steps SA10 to SA80 are executed until all projection data are the processing target.

5-4. Generation of Reconstructing Pixel for Generating Reconstruction Data by X-Ray CT (2)

Figure 14:
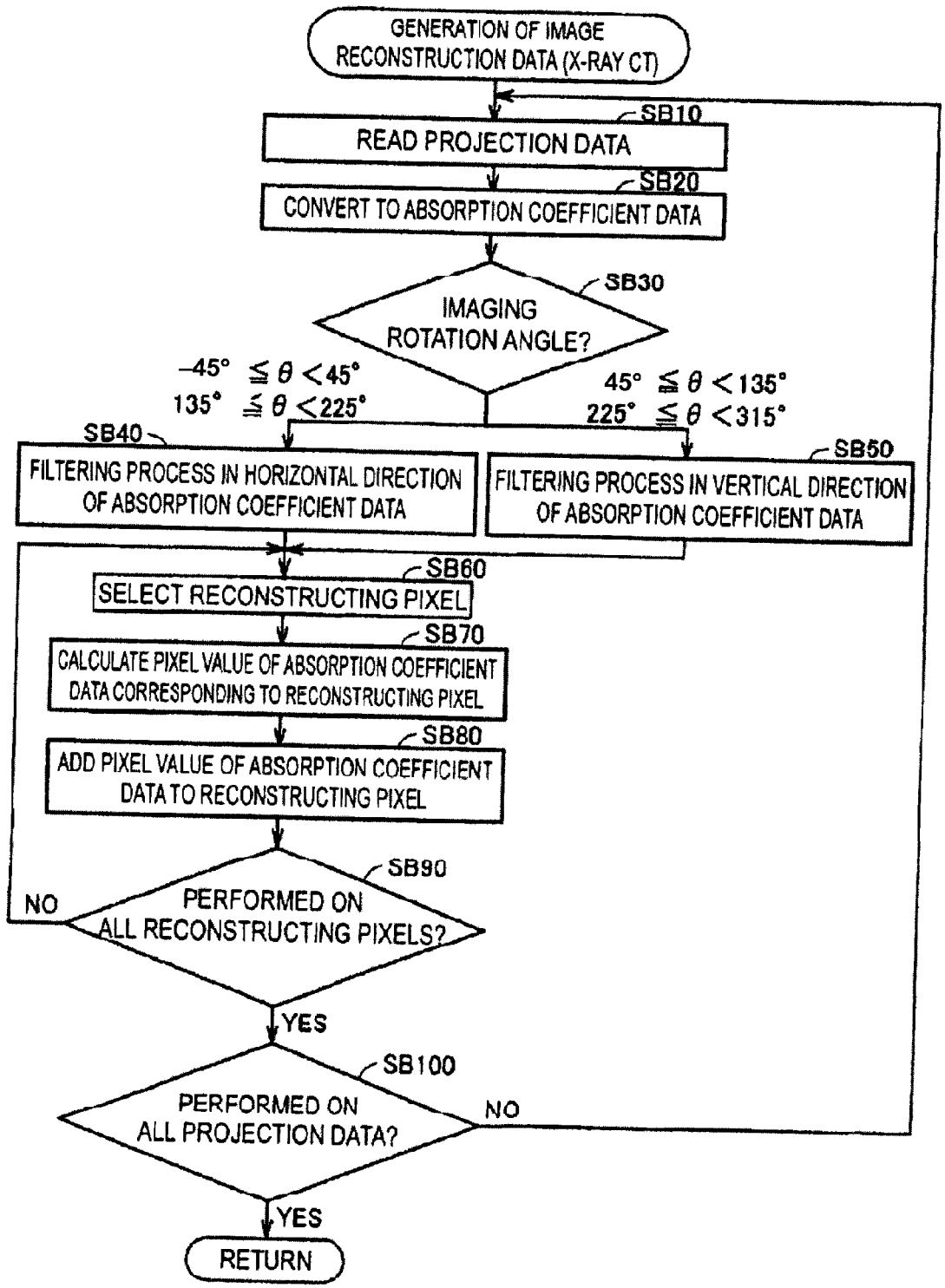
FIG. 14 is a flowchart of a variant of the process of FIG. 13.

FIG. 14 is a flowchart of a sub-routine of the process of generating the data of the reconstructing pixel for generating the reconstruction data by the X-ray CT in step S100, and is a flowchart of a variant of the process described in FIG. 13.

With reference to FIG. 14, in the relevant process, the calculation unit 70 first reads the projection data stored in the auxiliary storage unit 72 in step SB10, similar to step SA10, and proceeds the process to step SB20.

In step SB20, the calculation unit 70 converts the image data of each pixel of the projection data read in step SB10 to the absorption coefficient data, similar to step SA20, and proceeds the process to step SB30.

In step SB30, the calculation unit 70 determines the rotation angle on the virtual circle 300 of the FPD 3 when the projection data serving as the processing target is photographed. The calculation unit 70 proceeds the process to step SB40 if the position of the FPD 3 is in the rotation angle (from −45° to 45° and from 135° to 225° when the upper side of the intersection with the X-axis of the Y-axis is the reference) so as to be in the first quadrant or the third quadrant set in advance, as described with reference to FIG. 8, and proceeds the process to step SB50 if the position of the FPD 3 is in the rotation angle (from 45° to 135° and from 225° to 315° when the upper side of the intersection with the X-axis of the Y-axis is the reference) so as to be in the second quadrant or the fourth quadrant.

In step SB40, the calculation unit 70 performs the filtering process on the image data along the X-axis direction, as shown with respect to the first quadrant and the third quadrant of FIG. 8, and proceeds the process to step SB60.

In step SB50, the calculation unit 70 performs the filtering process on the image data along the Y-axis direction, as shown with respect to the second quadrant and the fourth quadrant of FIG. 8, and proceeds the process to step SB60.

In step SB60, one reconstructing pixel in the reconstruction data is selected, and the process proceeds to step SB70.

In step SB70, the calculation unit 70 calculates the absorption coefficient data and/or pixel value corresponding to the reconstructing pixel selected in step SB60 immediately before step SB 70 from the data subjected to the filtering process of step SB40, and proceeds the process to step SB80.

In step SB80, the pixel value calculated in step SB70 immediately before step SB80 is added to the pixel value, added up to this point for the reconstructing pixels selected in step SB60, and the process proceeds to step SB90.

In step SB90, the calculation unit 70 determines whether or not the processes of steps SB60 to SB80 are executed on all reconstructing pixels, and proceeds the process to step SB100 if determined as executed and returns the process to step SB60 if determined that the reconstructing pixel that is not yet the processing target exists.

Through the processes of steps SB60 to SB90, the pixel value is calculated on all reconstructing pixels constructing the reconstruction data with respect to the projection data of the processing target, and the calculated pixel value of each reconstructing pixel is added for every reconstructing pixel.

In step SB100, whether or not the processes of steps SB10 to SB90 are executed on all projection data stored in the auxiliary storage unit 72 is determined, and the process returns to FIG. 11 if determined as executed. If determined that the projection data that is not the processing target exists, the process returns to step SB10, and the processes of steps SB10 to SB90 are executed until all projection data are the processing target.

5-5. Generation of Reconstructing Pixel for Generating Reconstruction Data by X-Ray CT (3)

Figure 15:
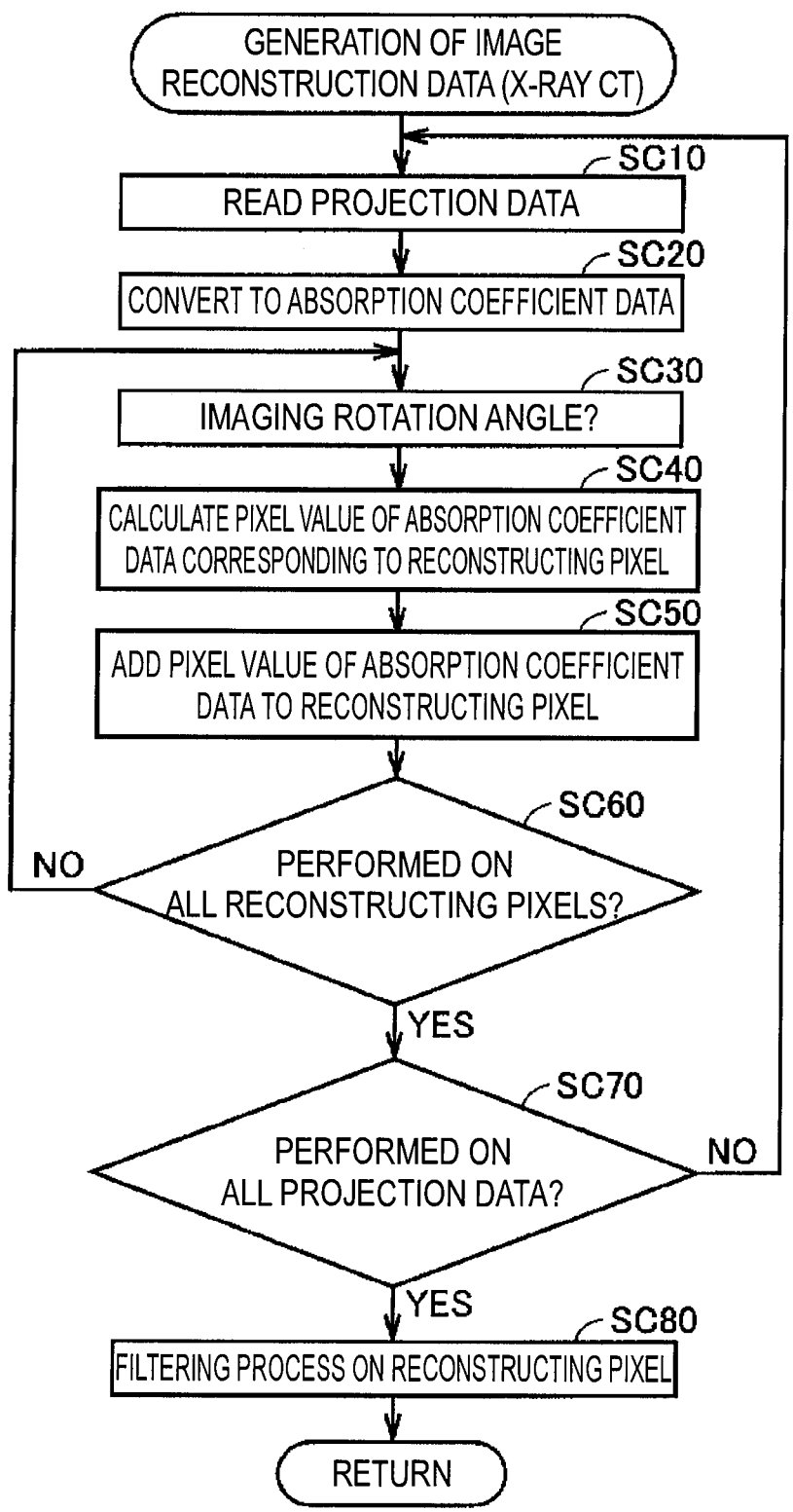
FIG. 15 is a flowchart of another variant of the process of FIG. 13.

FIG. 15 is a flowchart of a sub-routine of the process of generating the data of the reconstructing pixel for generating the reconstruction data by the X-Ray CT in step S100, and is a flowchart of a variant of the process described in FIG. 13.

With reference to FIG. 14, in the relevant process, the calculation unit 70 first reads the projection data stored in the auxiliary storage unit 72 in step SC10, similar to step SA10, and proceeds the process to step SC20.

In step SC20, the calculation unit 70 converts the image data of each pixel of the projection data read in step SC10 to the absorption coefficient data, similar to step SA20, and proceeds the process to step SC30.

In step SC30, the calculation unit 70 selects one reconstructing pixel in the reconstruction data, and proceeds the process to step SC40.

In step SC40, the calculation unit 70 calculates the absorption coefficient data and/or pixel value corresponding to the reconstructing pixel selected in step SC30 immediately before step SC40, and proceeds the process to step SC50.

In step SC50, the pixel value calculated in step SC40 immediately before step SC50 is added to the pixel value, added up to this point for the reconstructing pixels selected in step SC30, and the process proceeds to step SC60.

In step SC60, the calculation unit 70 determines whether or not the processes of steps SC30 to SC50 are executed on all reconstructing pixels, and proceeds the process to step SC70 if determined as executed and returns the process to step SC30 if determined that the reconstructing pixel that is not yet the processing target exists.

Through the processes of steps SC30 to SC60, the pixel value is calculated on all reconstructing pixels constructing the reconstruction data with respect to the projection data of the processing target, and the calculated pixel value of each reconstructing pixel is added for every reconstructing pixel.

In step SC70, whether or not the processes of steps SC10 to SC60 are executed on all projection data stored in the auxiliary storage unit 72 is determined, and the process proceeds to step S80 if determined as executed. If determined that the projection data that is not the processing target exists, the process returns to step SC10, and the processes of steps SC10 to SC60 are executed until all projection data are the processing target.

Figure 10C:
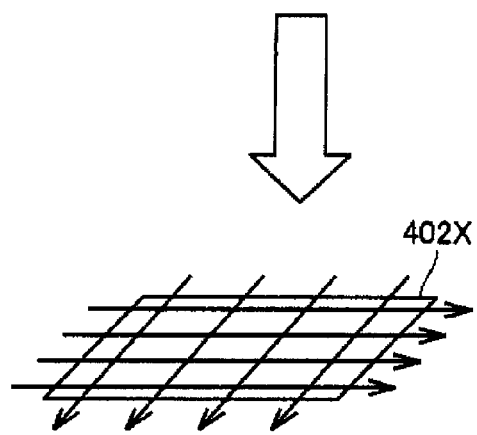

In step SC80, the calculation unit 70 temporarily generates the reconstruction data based on the reconstructing pixel obtained by the processes up to step SC90, as described with reference to FIGS. 10A to 10C, slices the reconstruction data for every predetermined interval, executes the filtering process on the data of each slice plane, and returns the process to the flowchart of FIG. 11.

In the present example, the final reconstruction data is generated by the reconstructing pixels ultimately obtained by processing all projection data.

In the present example, the reconstructing pixel constructing the temporarily reconstruction data corresponds to the first reconstructing pixel, and the reconstructing pixel constructing the final reconstruction data corresponds to the second reconstructing pixel.

5-6. Variant of Substrate Examination Process

Figure 16:
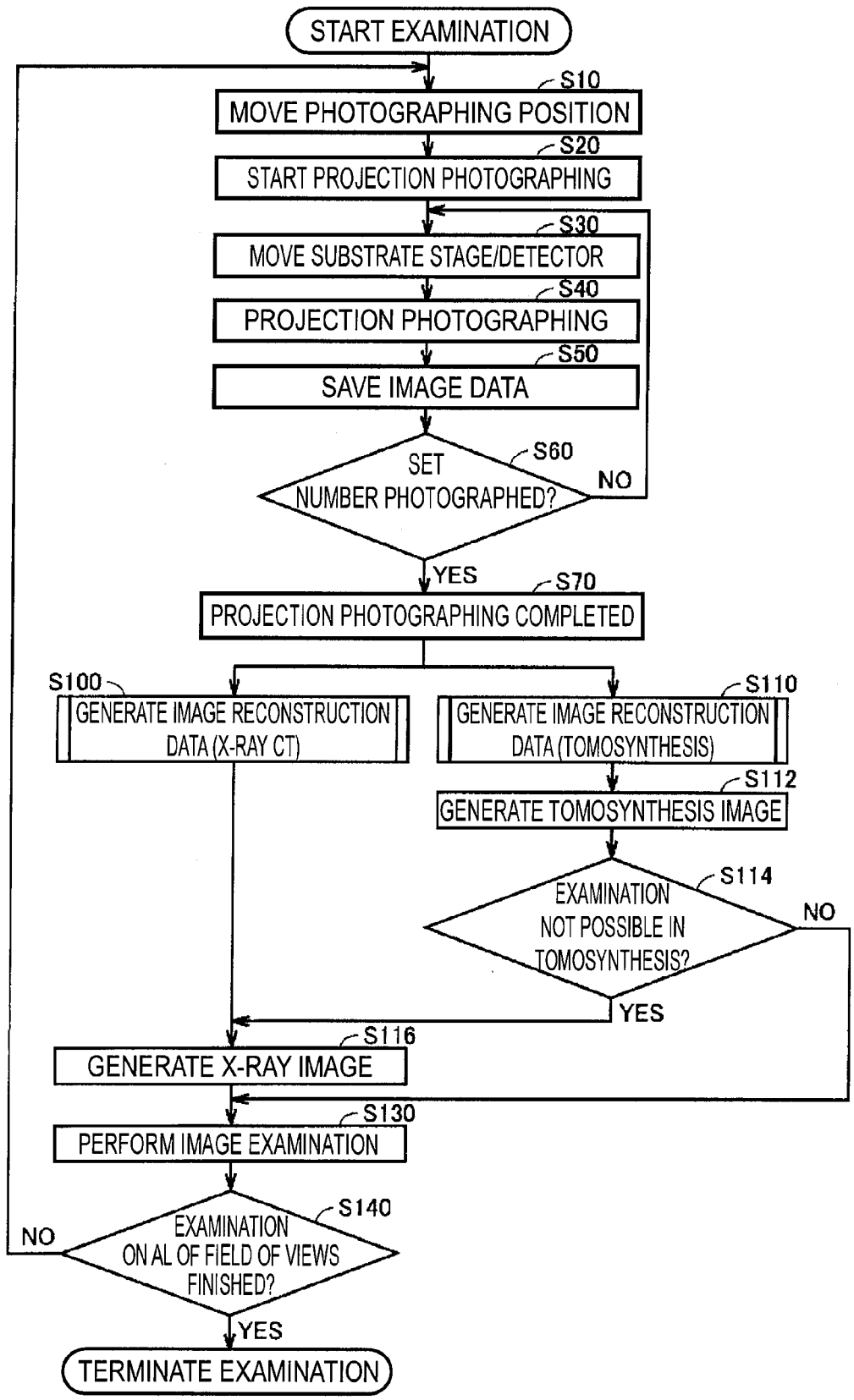
FIG. 16 is a flowchart of a variant of the substrate examination process of FIG. 11.

FIG. 16 is a flowchart of a variant of the substrate examination process shown in FIG. 11.

In the process described with reference to FIG. 11, the input of the information for selecting whether to have the reconstruction data as the X-ray CT image or the image of tomosynthesis is accepted in step S80 after the photographing of the projection is completed in step S70. In this variant, a process of generating the data of the reconstructing pixel by the X-ray CT and the data of the reconstructing pixel by the tomosynthesis starts in parallel in step S100 and step S110 after the photographing of the projection is completed in step S70 in the process of FIG. 11.

The calculation unit 70 executes the generation of the reconstruction data by the reconstructing pixel for tomosynthesis in step S112, and determines whether or not the generation of the reconstruction data by the tomosynthesis is possible in step S114.

If determined that the generation of the reconstruction data by the tomosynthesis is not possible in step S114, the calculation unit 70 generates the reconstruction data by the X-ray in step S116, executes the examination on the substrate 10 to be examined based on the reconstruction data by the X-ray CT in step S130, and proceeds the process to step S140.

If determined that the generation of the reconstruction data by the tomosynthesis is possible in step S114, the calculation unit 70 executes the examination on the substrate 10 to be examined based on the reconstruction data by the tomosynthesis in step S130, and proceeds the process to step S140.

In the present variant, if the generation of the reconstruction data by the tomosynthesis is possible, the generation of the reconstruction data by the X-ray CT that requires a long time since the filtering process or the like is required can be omitted, and the examination time can be reduced.

[6. Others]

Figure 17:
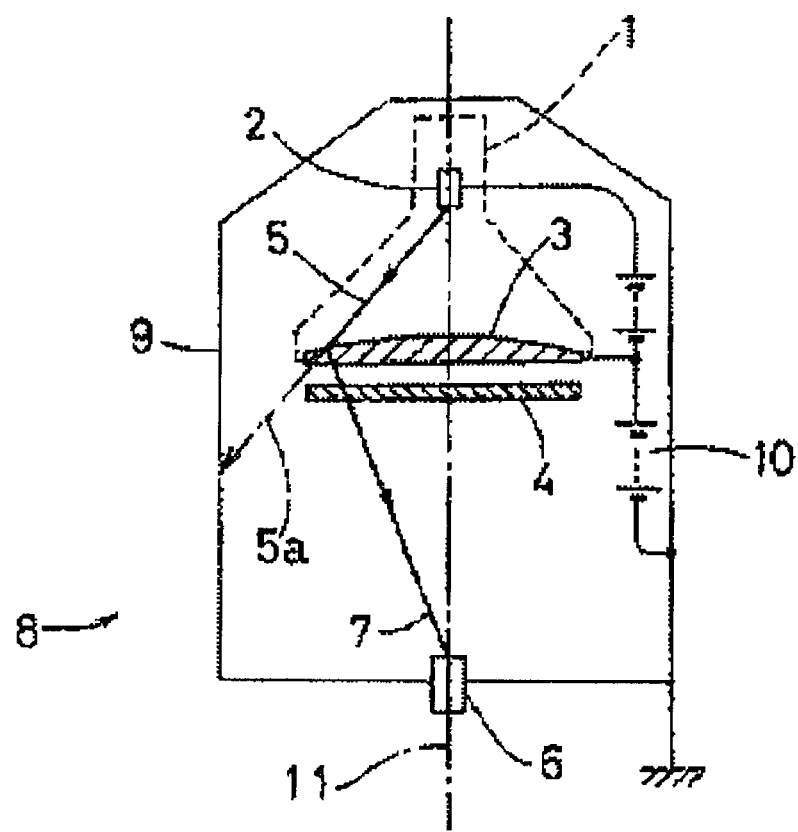
FIG. 17 is a view describing a construction of a conventional scanning X-ray tube.
Figure 18A:
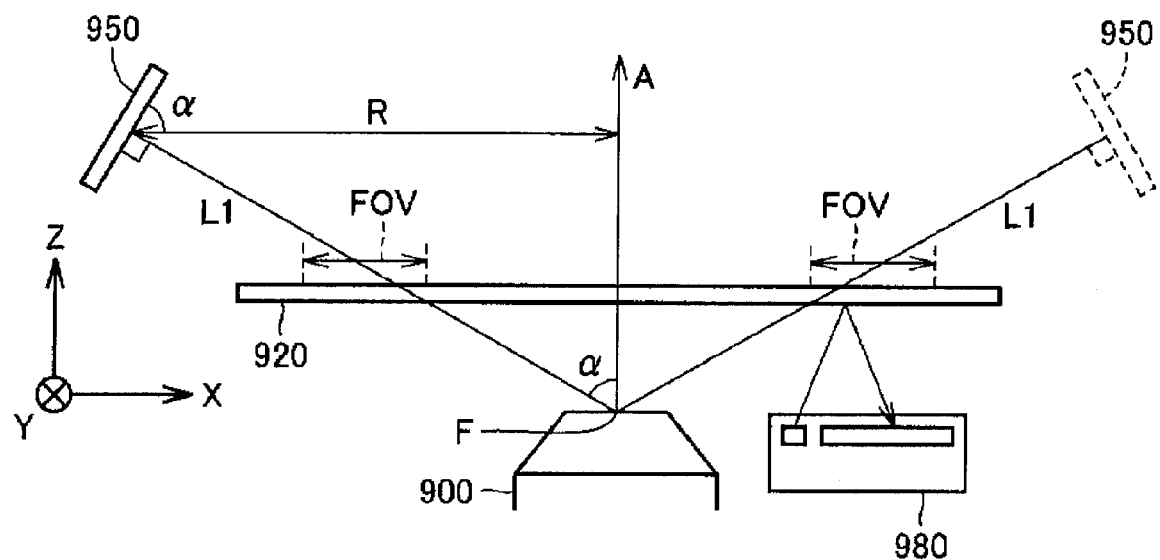
FIGS. 18A and 18B are views describing a mode of X-ray CT photographing in a conventional examination apparatus.
Figure 18B:
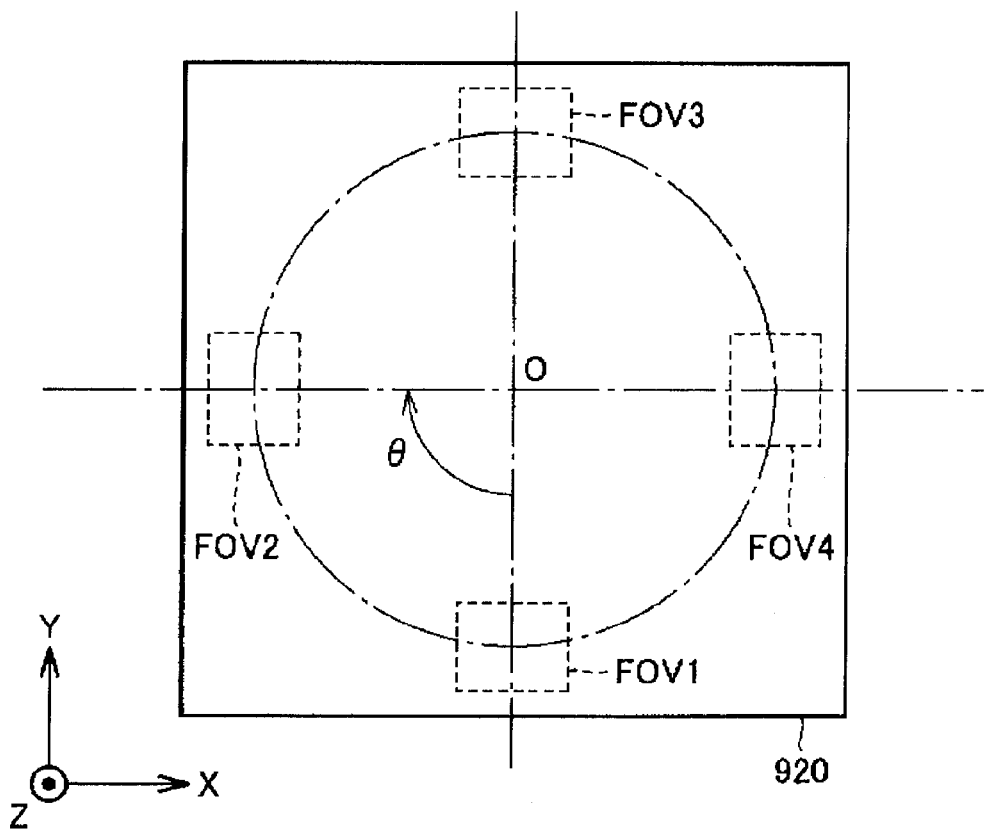
Figure 19:
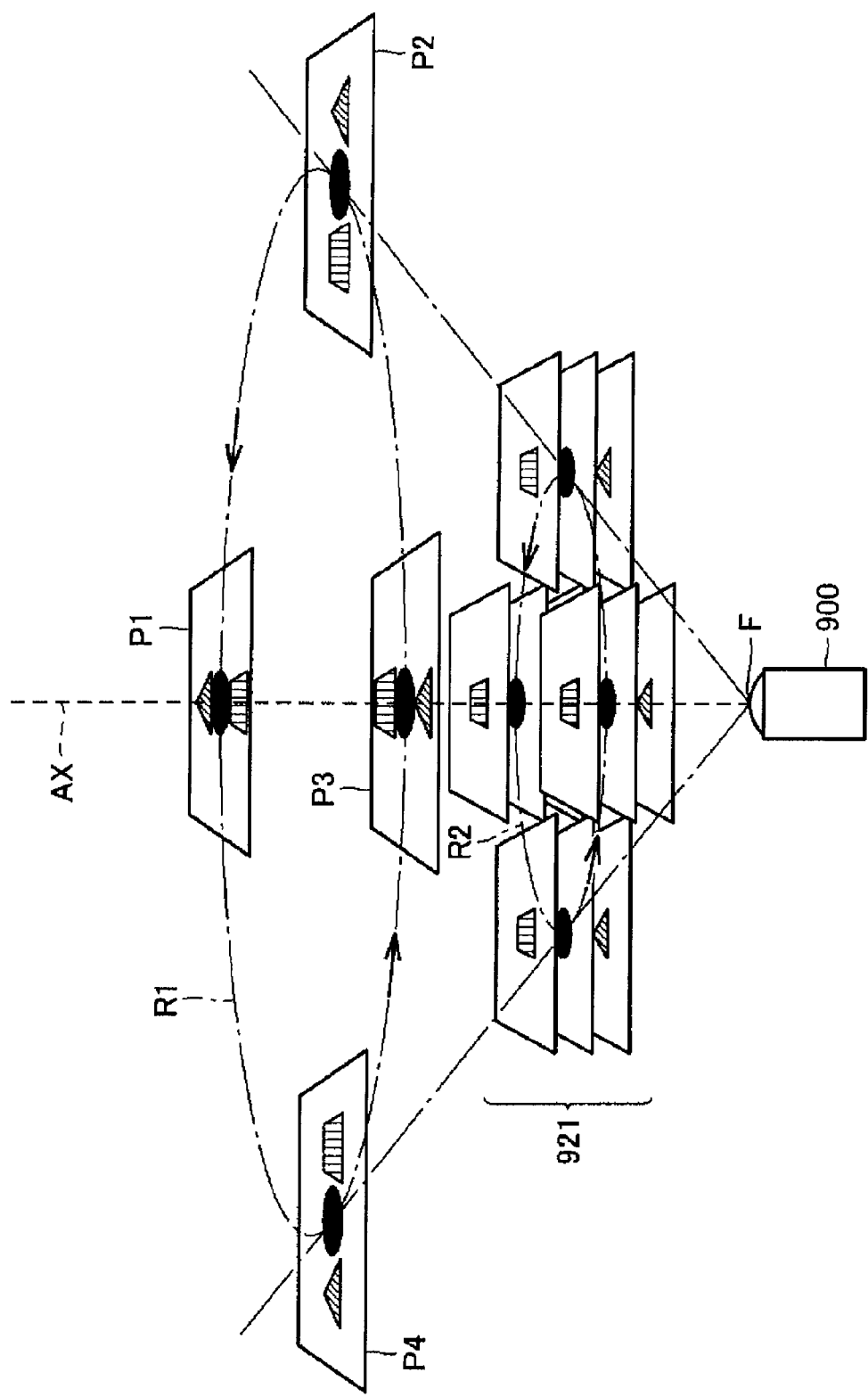
FIG. 19 is a view describing a mode of tomosynthesis photographing in the conventional examination apparatus.

In the present embodiment described above, the X-ray source is fixed, and the X-ray perspective image is photographed by moving the substrate and the detector using the substrate stage and the detector stage, respectively, but not limited thereto, an imaging position can be changed by mechanically moving the X-ray source using the X-ray source movement mechanism (not shown) without using either the substrate stage or the detector stage. This will be more specifically described with reference to FIG. 17. FIG. 17 is a cross-sectional view of the examination apparatus described in the conventional document (Japanese Unexamined Patent Publication No. 6-124671).

A scanning X-ray tube 1 shown in FIG. 17 scans the surface of the target 3 with the electron beam 5 generated by an electron gun 2, and generates the X-ray 7. The X-ray 7 in the same direction as the electron beam 5 transmitted through the target 3 of the X-rays generated by the target 3 is used. The X-ray 7 transmits through a non-examining object 4 and is detected by an X-ray detector 6. The reference numerals in the figure and the description comply with the reference numerals in the document of the prior art, and are not relevant to the reference numerals described in other areas.

An X-ray focal position can be moved through the use of the known scanning X-ray tube, and thus a position of the X-ray detector can be relatively changed on the circle having the optical axis of the X-ray source as the center without changing the position of the substrate or the FPD. The desired time in the X-ray scanning by the scanning X-ray source is far shorter than a mechanical position changing operation by the stage. In other words, the position of the FPD (X-ray detector) can be relatively changed if within the constant range without using either the substrate or the detector stage.

The substrate stage and the detector stage are used in the present embodiment from the standpoint of maintenance, reliability, and the like.

The embodiments disclosed herein are illustrative in all aspects and should not be recognized as exclusive. The scope of the invention is indicated by the Claims rather than by the description made above, and it should be apparent that all modifications equivalent in meaning to the Claims and within the scope of the invention are encompassed. The technical ideas described as variants such as the direction of the filtering process in the generation of the reconstruction data by the X-ray CT, the presence of rotation of the rotation data, and the like are intended to be implemented by being combined as much as possible.

What is claimed is:

1. An examination method for examining an examination target region of an examination object by capturing images from X-rays output of an X-ray source with an X-ray detection unit, the X-rays output being transmitted through the target region of the examination object, reconstructing a three-dimensional image of the examination target region based on the captured images, and examining the examination target region using the three-dimensional image obtained by the reconstruction, the method comprising the steps of:

changing a position of the X-ray detection unit along a circumference of a virtual circle, the X-ray source having an optical axis intersecting the center of the virtual circle, the optical axis being perpendicular to the surface of the virtual circle, the examination object being located away from the optical axis and between the X-ray source and the X-ray detection unit;

activating the X-ray detection unit to perform X-ray fluorography at each of a plurality of positions along the circumference of the virtual circle;

generating an X-ray computed tomography (CT) image based on the result of the X-ray fluorography by the X-ray detection unit; and generating a tomosynthetic tomographic image based on the same result of the X-ray fluorography as used for the generation of the X-ray computed tomography (CT) image, wherein the step of changing the position of the X-ray detection unit includes changing the position of the X-ray detection unit so that during the step of generating the X-ray computed tomography (CT) image, data of each pixel obtained as the result of the X-ray fluorography by the X-ray detection unit is subjected to a filtering process in a direction corresponding to a direction of one of two axes extending from the optical axis, the two axes are orthogonal to each other and both intersecting and orthogonal to the optical axis of the virtual circle, and the filtering process takes place at one or more of the plurality of positions along the circumference of the virtual circle.

2. The examination method according to claim 1, wherein in the step of generating the X-ray computed tomography (CT) image, data of each pixel obtained as the result of the X-ray fluorography by the X-ray detection unit is subjected to a filtering process in a direction tangential to the virtual circle.

3. The examination method according to claim 1, wherein in the step of generating the X-ray computed tomography (CT) image, data of each pixel obtained as a result of the X-ray fluorography by the X-ray detection unit at a first position of the plurality of positions replaces data of a pixel obtained as a result of the X-ray fluorography by the X-ray detection unit at a second position of the plurality of positions based on an angle of rotation of the X-ray detection unit about the optical axis between the first position and the second position, before subjecting the data to the filtering process.

4. The examination method according to claim 1, wherein an angle of rotation of the X-ray detection unit about the optical axis between each of the plurality of positions is constant and the direction of the filtering process is determined based on the angle of rotation.

5. The examination method according to claim 1, wherein the step of generating the X-ray computed tomography (CT) image further includes the steps of:

generating a first reconstructing pixel based on the result of the X-ray fluorography by the X-ray detection unit, generating a second reconstructing pixel by performing a filtering process on the first reconstructing pixel, and generating the three-dimensional image based on the second reconstructing pixel.

6. An examination apparatus for examining an examination target region of an examination object by capturing images from X-rays output of an X-ray source with an X-ray detection unit, the X-rays output being transmitted through the target region of the examination object, reconstructing a three-dimensional image of the examination target region based on the captured images, and examining the examination target region using the three-dimensional image obtained by the reconstruction, the examination apparatus comprising:

a first stage for holding an examination object;

a first movement mechanism with drive shafts, each drive shaft being configured to orientate the first stage relative to one of two directions;

an X-ray source arranged above or beneath the first stage, the X-ray source having an optical axis perpendicular to the two directions;

an X-ray detection unit;

a second stage for holding the X-ray detection unit;

a second movement mechanism with drive shafts configured to move the second stage along a circumference of a virtual circle; and a control unit configured to:

control changing of a position of the X-ray detection unit along the circumference of the virtual circle, the X-ray source having an optical axis intersecting the center of the virtual circle, the optical axis being perpendicular to the surface of the virtual circle, the examination object being located away from the optical axis and between the X-ray source and the X-ray detection unit;

activate the X-ray detection unit to perform X-ray fluorography at each of a plurality of positions along the circumference of the virtual circle;

generate an X-ray computed tomography (CT) image based on the result of the X-ray fluorography by the X-ray detection unit; and generate a tomosynthetic tomographic image based on the same result of the X-ray fluorography as used for the generation of the X-ray computed tomography (CT) image, wherein the step of changing the position of the X-ray detection unit includes changing the position of the X-ray detection unit so that during the step of generating the X-ray computed tomography (CT) image, data of each pixel obtained as the result of the X-ray fluorography by the X-ray detection unit is subjected to a filtering process in a direction corresponding to a direction of one of two axes extending from the optical axis, the two axes are orthogonal to each other and both intersecting and orthogonal to the optical axis of the virtual circle, and the filtering process takes place at one or more of the plurality of positions along the circumference of the virtual circle.

7. A non-transitory machine-readable medium, having stored thereon machine-readable instructions for executing, by a machine, an examination method for examining an examination target region of an examination object by capturing images from X-rays output of an X-ray source with an X-ray detection unit, the X-rays output being transmitted through the target region of the examination object, reconstructing a three-dimensional image of the examination target region based on the captured images, and examining the examination target region using the three-dimensional image obtained by the reconstruction, the method comprising the steps of:

changing a position of the X-ray detection unit along a circumference of a virtual circle, the X-ray source having an optical axis intersecting the center of the virtual circle, the optical axis being perpendicular to the surface of the virtual circle, the examination object being located away from the optical axis and between the X-ray source and the X-ray detection unit;

activating the X-ray detection unit to perform X-ray fluorography at each of a plurality of positions along the circumference of the virtual circle;

generating an X-ray computed tomography (CT) image based on the result of the X-ray fluorography by the X-ray detection unit; and generating a tomosynthetic tomographic image based on the same result of the X-ray fluorography as used for the generation of the X-ray computed tomography (CT) image, wherein the step of changing the position of the X-ray detection unit includes changing the position of the X-ray detection unit so that during the step of generating the X-ray computed tomography (CT) image, data of each pixel obtained as the result of the X-ray fluorography by the X-ray detection unit is subjected to a filtering process in a direction corresponding to a direction of one of two axes extending from the optical axis, the two axes are orthogonal to each other and both intersecting and orthogonal to the optical axis of the virtual circle, and the filtering process takes place at one or more of the plurality of positions along the circumference of the virtual circle.

8. The examination method according to claim 1, wherein the filtering process takes place at each of the plurality of positions along the circumference of the virtual circle.

* * * * *